(12) United States Patent
Won et al.

(10) Patent No.: US 11,468,978 B2
(45) Date of Patent: Oct. 11, 2022

(54) REFRIGERATOR, TERMINAL, AND METHOD OF CONTROLLING THE SAME

(71) Applicant: Samsung Electronics Co., Ltd, Suwon-si (KR)

(72) Inventors: Sang Chul Won, Suwon-si (KR); Taek Woon Kim, Seongnam-si (KR); Hani Yang, Gwangmyeong-si (KR); Min Jin Song, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 852 days.

(21) Appl. No.: 16/383,210

(22) Filed: Apr. 12, 2019

(65) Prior Publication Data

US 2019/0237183 A1 Aug. 1, 2019

Related U.S. Application Data

(62) Division of application No. 14/555,389, filed on Nov. 26, 2014, now abandoned.

(30) Foreign Application Priority Data

Dec. 11, 2013 (KR) .......................... 10-2013-0154150

(51) Int. Cl.
*G16H 20/60* (2018.01)
*G06Q 10/10* (2012.01)
(Continued)

(52) U.S. Cl.
CPC ............. *G16H 20/60* (2018.01); *F25D 29/00* (2013.01); *G06Q 10/10* (2013.01); *G06Q 50/10* (2013.01);
(Continued)

(58) Field of Classification Search
CPC ........ G16H 20/60; G16H 10/10; G16H 50/30; G06Q 10/10; G06Q 50/10; F25D 2400/361; F25D 29/00; F25D 2500/06
See application file for complete search history.

(56) References Cited

U.S. PATENT DOCUMENTS 6,587,739 B1    7/2003  Abrams et al.
6,892,545 B2 *  5/2005  Ishikawa .................. B65D 5/42
                                              62/126
(Continued)

FOREIGN PATENT DOCUMENTS

KR    10-2006-0018408 A    3/2006
KR    10-2006-0120799 A    11/2006
(Continued)

OTHER PUBLICATIONS

Office Action dated Oct. 29, 2020 in connection with Korean Patent Application No. 10-2013-0154150, 7 pages.
(Continued)

*Primary Examiner* — Michael Collins

(57) ABSTRACT

There is provided a refrigerator, including an input unit configured to receive information on a user, the user's health information, and an examination time; a control unit configured to perform control such that the received user information and health information are stored and displayed, identify a reception time at which the health information is received, and perform control such that at least one time of the examination time and the reception time is stored and displayed; a storage unit configured to accumulate and store the user's health information and examination time and match the user information and the health information for each examination time and store; and a display unit configured to display the health information in order of the examination time. According to the present disclosure, since a health state is determined according to accumulated health (Continued)

information and the determined health state is displayed through the display unit, the user is continuously informed of the health state and is well aware of health. Further, the user may improve eating habits to prevent and manage various types of diseases.

11 Claims, 29 Drawing Sheets

(51) Int. Cl.
  *G06Q 50/10* (2012.01)
  *F25D 29/00* (2006.01)
  *G16H 50/30* (2018.01)

(52) U.S. Cl.
  CPC ....... *G16H 50/30* (2018.01); *F25D 2400/361* (2013.01); *F25D 2500/06* (2013.01)

(56) References Cited

U.S. PATENT DOCUMENTS

| | | | |
|---|---|---|---|
| 9,057,554 B2* | 6/2015 | Quinlan | G05B 19/0428 |
| 9,074,806 B2 | 7/2015 | Cheon et al. | |
| 9,195,960 B2* | 11/2015 | Kim | G06Q 10/087 |
| 2002/0157411 A1* | 10/2002 | Ishikawa | F25D 29/005 |
| | | | 62/331 |
| 2004/0035123 A1 | 2/2004 | Kim et al. | |
| 2005/0160005 A1 | 7/2005 | Roth et al. | |
| 2006/0122532 A1 | 6/2006 | Lee et al. | |
| 2006/0224050 A1 | 10/2006 | Lee et al. | |
| 2007/0167692 A1 | 7/2007 | Kim | |
| 2008/0184719 A1 | 8/2008 | Lowenstein | |
| 2008/0195944 A1 | 8/2008 | Lee et al. | |
| 2010/0058792 A1* | 3/2010 | Seo | F25D 11/02 |
| | | | 62/264 |
| 2010/0283573 A1* | 11/2010 | Yum | G05B 15/02 |
| | | | 340/3.1 |
| 2010/0283601 A1* | 11/2010 | Tai | A61J 7/0409 |
| | | | 340/539.12 |
| 2011/0318717 A1 | 12/2011 | Adamowicz | |
| 2012/0041577 A1 | 2/2012 | Cho et al. | |
| 2012/0137706 A1 | 6/2012 | Hussain et al. | |
| 2012/0217254 A1* | 8/2012 | Cho | F25D 29/00 |
| | | | 220/592.02 |
| 2012/0260683 A1 | 10/2012 | Cheon et al. | |
| 2013/0095459 A1 | 4/2013 | Tran | |
| 2013/0138656 A1 | 5/2013 | Wheaton | |
| 2013/0214935 A1* | 8/2013 | Kim | G08C 17/02 |
| | | | 340/870.02 |
| 2013/0262995 A1 | 10/2013 | Howell | |
| 2013/0280681 A1 | 10/2013 | Narayan et al. | |
| 2014/0006131 A1 | 1/2014 | Causey et al. | |
| 2014/0095479 A1 | 4/2014 | Chang et al. | |
| 2014/0180847 A1 | 6/2014 | Silverstein et al. | |
| 2014/0252091 A1 | 9/2014 | Morse et al. | |
| 2014/0358287 A1 | 12/2014 | Lee et al. | |
| 2015/0294451 A1 | 10/2015 | Lee et al. | |
| 2017/0270474 A1* | 9/2017 | McCoy | G06Q 50/22 |
| 2019/0075200 A1* | 3/2019 | Seo | G06F 1/1698 |

FOREIGN PATENT DOCUMENTS

| | | |
|---|---|---|
| KR | 10-2007-0010379 A | 1/2007 |
| KR | 10-2012-0116207 A | 10/2012 |
| KR | 10-2012-0118376 A | 10/2012 |

OTHER PUBLICATIONS

Office Action dated Apr. 23, 2020 in connection with Korean Patent Application No. 10-2013-0154150, 19 pages.

* cited by examiner

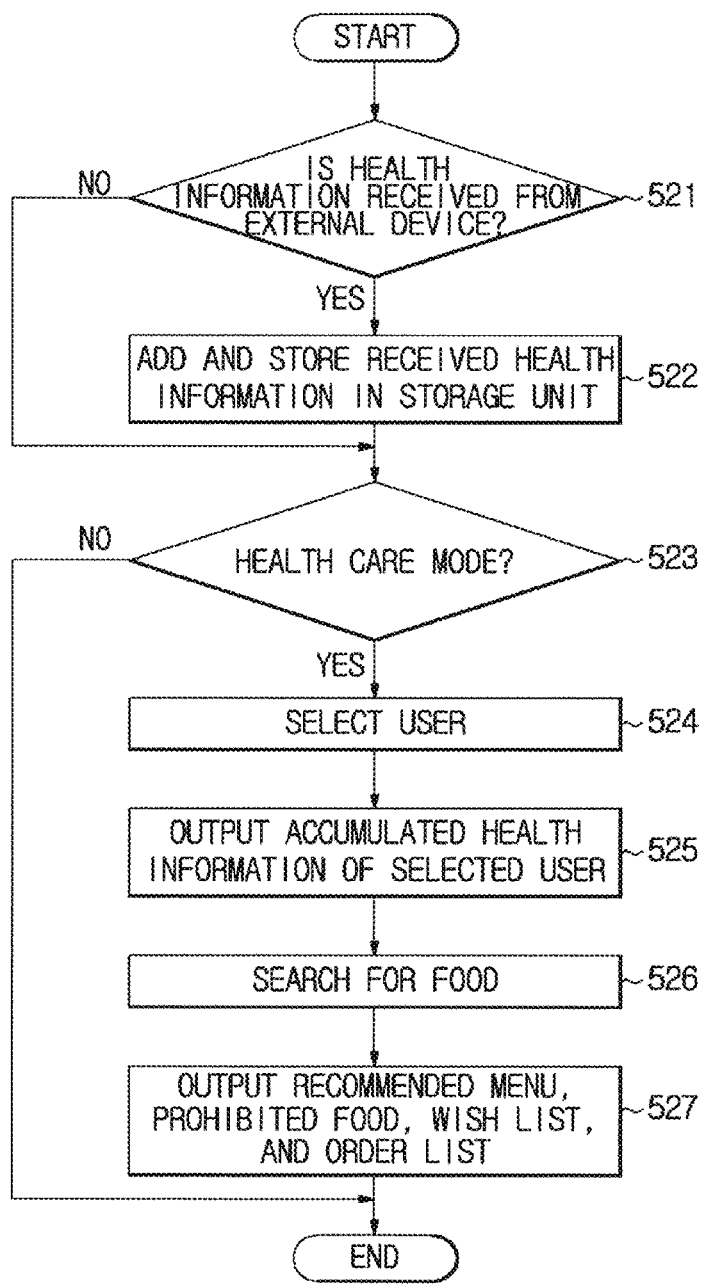

REFRIGERATOR, TERMINAL, AND METHOD OF CONTROLLING THE SAME

CROSS-REFERENCE TO RELATED APPLICATIONS

This application is a divisional of U.S. patent application Ser. No. 14/555,389 filed on Nov. 26, 2014, which is based on and claims priority to Korean Patent Application No. 10-2013-0154150 filed on Dec. 11, 2013, the disclosures of which are herein incorporated by reference in their entirety.

BACKGROUND

1. Field

The present disclosure relates to a refrigerator configured to output information on a user's health information and food, a terminal configured to transmit the health information to the refrigerator, and a method of controlling the same.

2. Description of Related Art

A refrigerator is a device for keeping storage items such as food and beverages fresh for a long time.

The refrigerator has a plurality of storage containers. The plurality of storage containers include a freezer unit for frozen storage of a storage item and a refrigerator unit for cold storage of a storage item. The refrigerator repeats a freezing cycle including compression-condensation-expansion-evaporation and maintains interior temperatures of the freezer unit and the refrigerator unit to each set target temperature.

Also, a temperature in the refrigerator unit, a temperature in the freezer unit, and the like are displayed through a display provided in the refrigerator such that a user may recognize the interior temperature.

The user takes out and uses food stored in the refrigerator as necessary. Also, the user identifies types of food in the refrigerator and then buys necessary food or insufficient food again. Then, the user sees food stored in the refrigerator individually and identifies an expiration date.

According to such a refrigerator, since it is unable to accurately identify food stored in the refrigerator, there are inconveniences that the user should identify individually and also identify an expiration date of storage food individually.

Also, as obesity is rapidly increasing due to changes in a living environment and eating habits, an interest in health increases accordingly.

Needless to say, obesity itself is not dangerous but it is generally risky when visceral fat becomes excessive and an abdominal fat ratio increases, which cause a very high occurrence rate of hypertension, cardiovascular disease, and the like.

SUMMARY

To address the above-discussed deficiencies, it is a primary object to provide disclosure a refrigerator that stores and displays a user's health information input to a user interface in order of an examination time, and a method of controlling the same.

The present disclosure also provides a refrigerator that stores and displays a user's health information transmitted from an external device in order of an examination time, and a method of controlling the same.

The present disclosure also provides a refrigerator that provides at least one of a recommended dish menu, prohibited food, and a wish list of food based on a user's health information, and a method of controlling the same.

The present disclosure also provides a terminal that transmits health information to a refrigerator.

According to an aspect of the present disclosure, there is provided a refrigerator. The refrigerator includes an input unit configured to receive information on a user, the user's health information, and an examination time; a control unit configured to perform control such that the received user information and health information are stored and displayed, identify a reception time at which the health information is received, and perform control such that at least one time of the examination time and the reception time is stored and displayed. The refrigerator also includes a storage unit configured to accumulate and store the user's health information and examination time and match the user information and the health information for each examination time and store. The refrigerator further includes a display unit configured to display the health information in order of the examination time.

The refrigerator includes a communication unit configured to receive the user's health information and examination time transmitted from an external device. The control unit performs control such that the user's health information and examination time being received are matched and stored and perform control such that the user's health information is displayed in order of the examination time.

The control unit matches the reception time and the health information when the examination time is not received.

The control unit performs control such that the health information stored in the storage unit is compared in order of the examination time, a change in his or her health state corresponding to a time change is analyzed, and a change in the analyzed health state is displayed.

The refrigerator includes a storage container configured to store food. The input unit receives food information of food to be stored in the storage container, and the storage unit stores the received food information.

The input unit receives a storage location of food to be stored in the storage container, and the storage unit matches the food information and the received storage location and store.

The control unit generates a recommended dish menu based on the user's current health state and the stored food information.

The control unit identifies an expiration date in the stored food information and generates a recommended dish menu based on the expiration date of the identified food.

The control unit determines a display priority of the recommended dish menu based on an expiration date of food used for each recommended dish of the generated recommended dish menu.

The control unit identifies prohibited food based on the user's health information and health state being stored, the food information stored in the storage unit, and control display of the identified prohibited food.

The input unit receives deletion of information on food removed from the storage container, and the storage unit deletes information on food of which removal is received from the stored food information.

The control unit identifies food used for the recommended dish, compares the identified food with the stored food information, identifies food that is not in the storage container among the identified food, adds the identified food to a wish list, and controls display of the wish list.

The refrigerator further includes a communication unit configured to communicate with a food server. The control unit performs control such that the communication unit transmits an order list selected by the user among the wish list to the food server.

The control unit receives food information transmitted from the food server and control storage of the received food information.

The control unit analyzes the received food information and recommend a storage location for each food.

According to another aspect of the present disclosure, there is provided a method of controlling a refrigerator having a user interface unit. The method includes receiving information on a user. The method also includes receiving the user's health information and an examination time. The method further includes matching the user's health information and examination time being received and storing. The method includes displaying the user's health information in order of the examination time. The method also includes comparing the stored health information in order of the examination time and analyzing and displaying a change in the user's health state. The method further includes generating a recommended dish menu based on the analyzed change in the health state and food stored in a storage container. The method includes displaying the generated recommended dish menu.

The method further includes receiving the user's health information and an examination time transmitted from an external device, and matching the user's health information and examination time being received, and storing.

The method further includes matching a reception time at which the health information is received and the health information and storing, when the examination time is not received in reception of the health information from the external device.

The method further includes receiving food information and a storage location of food to be stored in the storage container, and matching the received food information and storage location, and storing.

The method further includes receiving food information and a storage location of food to be stored in the storage container, and matching the received food information and storage location, and storing.

The generating of the recommended dish menu includes identifying an expiration date among the stored food information, generating a recommended dish menu based on the identified expiration date of food, and displaying the generated recommended dish menu.

The displaying of the generated recommended dish menu includes identifying food used for each recommended dish in the generated recommended dish menu, identifying an expiration date of the identified food, and determining a display priority of the recommended dish menu such that a recommended dish menu made of food having the shortest expiration date among the identified expiration dates is set to have top priority.

The method further includes identifying prohibited food based on the user's health information and health state being stored, and food information stored in the storage unit, and displaying the identified prohibited food.

The method further includes receiving deletion of information on food removed from the storage container, and deleting information on food of which removal is received from the stored food information.

The method further includes identifying food used for the recommended dish menu, comparing the identified food with the stored food information and identifying food that is not in the storage container among the identified food, and adding the identified food to a wish list and storing, and displaying the wish list.

The method further includes transmitting food selected by the user among the wish list to the food server.

According to still another aspect of the present disclosure, there is provided a terminal. The terminal includes an examination unit configured to examine a user's health. The terminal also includes a control unit configured to control transmission of examined health information and an examination time. The terminal further includes a communication unit configured to transmit the health information and the examination time to a refrigerator.

The terminal furthers include an input unit configured to receive at least one of the examination time and the user information. The terminal also includes a display unit configured to display the examined health information and the examination time.

According to the aspect, since a health state is determined according to accumulated health information and the determined health state is displayed through the display unit, the user is continuously informed of the health state and is well aware of health. Further, the user may improve eating habits to prevent and manage various types of diseases.

Also, by displaying an optimal dish menu and information on food that is appropriate for the user and to which the user's preference, constitution, health state, and the like are reflected, the user may eat food according to individual health and constitution and promote health.

Also, since an optimal diet is selected and displayed, it is possible to manage a blood glucose level, a blood pressure, and obesity with ease. Further, by providing a dish appropriate for diabetes that may be easily caused by obesity and the like, it is possible to prevent and manage diabetes, hypertension or hypotension, thereby promoting health.

Also, since health information is accumulated and stored, a health state is managed and analyzed for each period, and further, since a change in the health state and a next health examination time are displayed, it is possible to continuously manage health.

Also, a list of recommended dish menus is generated based on an expiration date of food, and recipe information corresponding to the recommended dish menu is displayed and provided for the user, thereby improving utility for the user.

Also, the user directly inputs health information, or the user's health information is received from a terminal and a medical device serving as an external device, and the user's health information is managed. Therefore, since there is a reduced need to provide a health examination device to the refrigerator, it is possible to reduce a manufacturing cost of the refrigerator.

Also, since information on food stored therein may be identified from the outside the refrigerator without identifying food in the refrigerator by opening a door of the refrigerator, convenience for the user may increase.

Also, by providing a grocery manager through a display such that a storage location, an expiration date, and the like of food stored in the refrigerator may be easily recognized, it is possible to efficiently manage stored food.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 23 illustrates a control process of a refrigerator according to still another embodiment.

DETAILED DESCRIPTION

FIGS. 1 through 23, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system and method. Hereinafter, the present disclosure will be described in detail with reference to the accompanying drawings.

Figure 1:
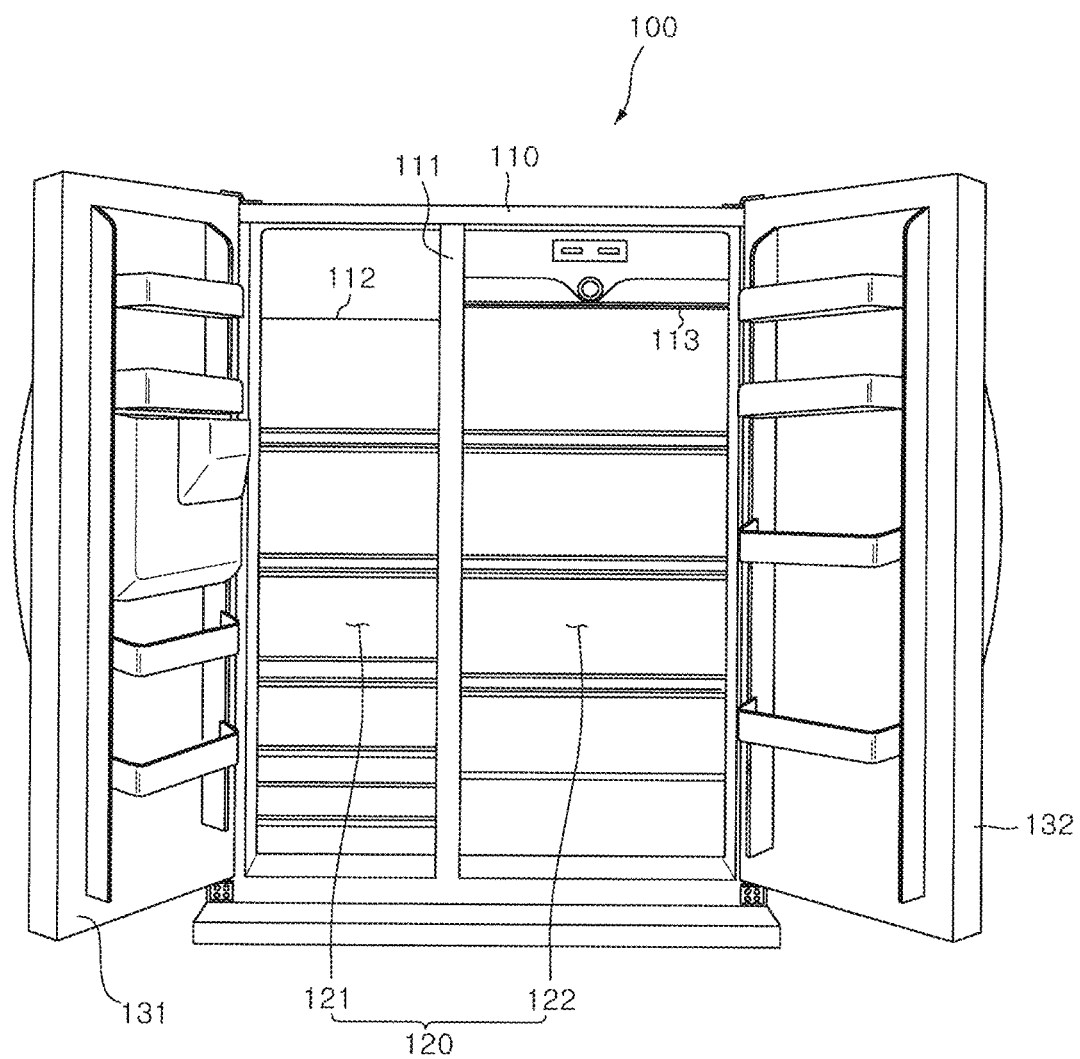
FIG. 1 illustrates a diagram showing an example inside of a refrigerator according to an embodiment.
Figure 2:
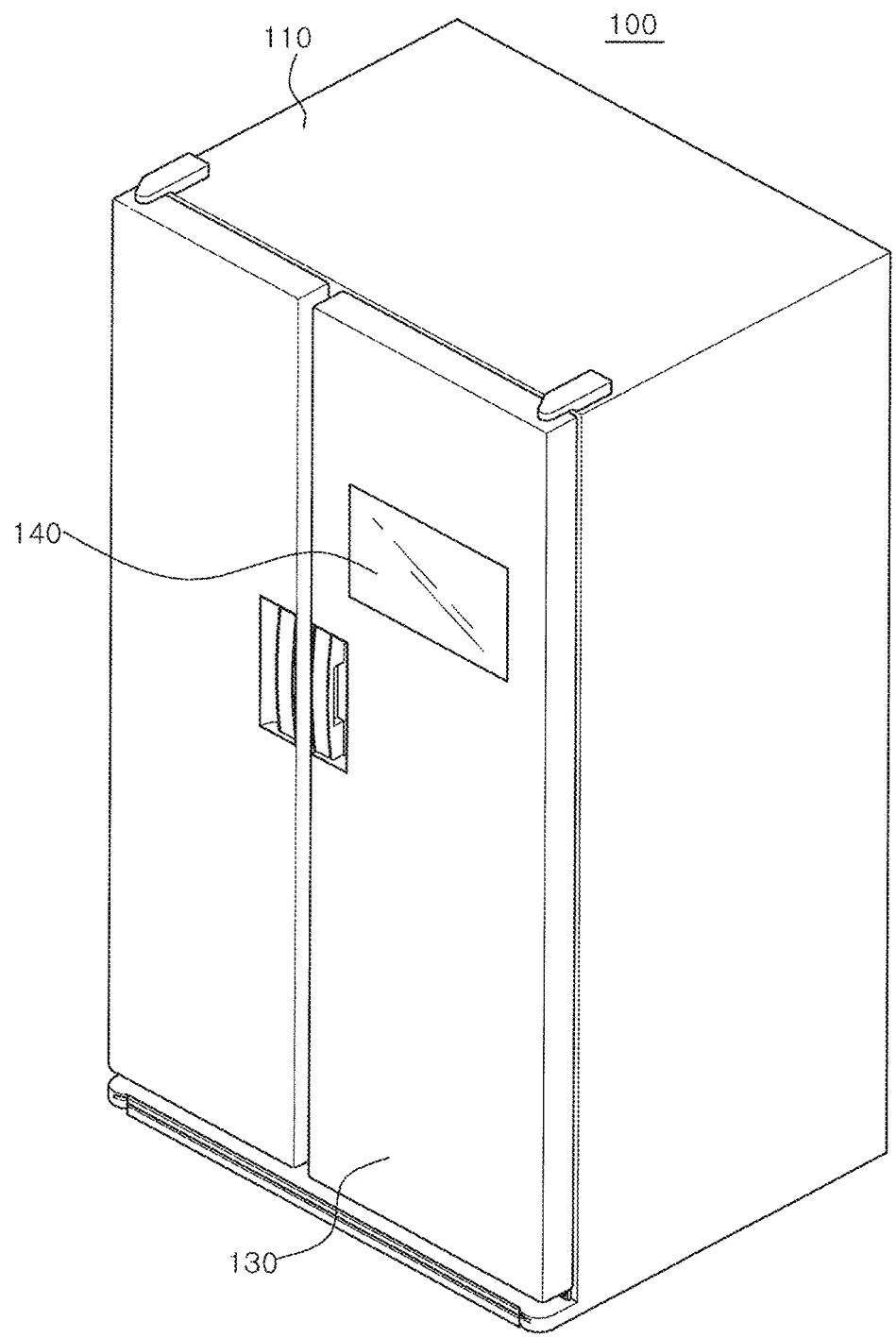
FIG. 2 illustrates a diagram showing an example front of a refrigerator according to an embodiment.

FIG. 1 illustrates a diagram showing an example inside of a refrigerator according to an embodiment. FIG. 2 illustrates a diagram showing an example front of a refrigerator according to an embodiment.

As illustrated in FIG. 1, a refrigerator 100 includes a main body 110, storage containers 120: 121 and 122, and doors 130: 131 and 132.

The main body 110 forms an appearance of the refrigerator 100.

The refrigerator has an accommodation space formed by the main body 110.

An intermediate partition wall 111 is provided in this accommodation space. The intermediate partition wall 111 divides the accommodation space of the main body 110 into left and right spaces. The accommodation space that is divided into left and right spaces in the main body 110 in this manner forms a plurality of storage containers 120: 121 and 122 for storing food.

The plurality of storage containers 120 include the freezer unit 121 serving as a first storage container for frozen storage of food and the refrigerator unit 122 serving as a second storage container for cold storage of food.

In addition, the freezer unit 121 may also include an ice-making unit (not illustrated) for making ice.

A plurality of holes (not illustrated) is formed in an inner wall surface of the main body 110 forming the freezer unit 121. The plurality of holes are holes configured to introduce cool air that is heat-exchanged in an evaporator into the freezer unit 121 and discharge the cool air of the freezer unit to the evaporator.

In addition, the freezer unit 121 may also include at least one shelf 112 for storing food.

A plurality of holes is formed in an inner wall surface of the main body 110 forming the refrigerator unit 122. The plurality of holes are holes configured to introduce cool air that is heat-exchanged in an evaporator into the refrigerator unit 122 and discharge the cool air of the refrigerator unit to the evaporator.

Shelves 113 and storage boxes for storing food are included in the refrigerator unit 122.

The refrigerator includes the door 130 that opens and closes an opening of the main body 110.

Fronts of the plurality of storage containers including the freezer unit 121 and the refrigerator unit 122 are open. The doors 130: 131 and 132 are pivotally installed in the fronts that are openings of the freezer unit 121 and the refrigerator unit 122, respectively.

The doors 130: 131 and 132 shield the freezer unit 121 and the refrigerator unit 122 from the outside. In addition, the doors 131 and 132 include a plurality of door shelves for storing food.

The refrigerator further includes a freezing cycle unit (not illustrated) formed in a space between inner walls of the main body 110.

The evaporator of the freezing cycle unit is provided in a rear surface of one of the storage containers, and when a decompressed refrigerant is provided from a capillary, cools surrounding air by a cooling operation in which surrounding latent heat is absorbed and provides a gaseous refrigerant to a compressor again.

The refrigerator further includes a first fan that is provided to correspond to the evaporator and applies wind power to cool air such that air of the freezer unit 121 and the refrigerator unit 122 is vacuumed, and air that has passed through the evaporator is discharged to the freezer unit 121 and the refrigerator unit 122.

The compressor, a condenser, and the capillary of the freezing cycle unit are provided in a machine room.

The machine room includes the compressor configured to compress the refrigerant and discharge the refrigerant in a high temperature and high pressure state, the condenser configured to condense the refrigerant of the high temperature and high pressure state that is compressed by the compressor through heat radiation, the capillary configured to decompress the refrigerant that is condensed by the condenser, and a second fan configured to cool the condenser.

Here, the capillary is connected to the evaporator and provides the decompressed refrigerant to the evaporator. In addition, an expansion valve may be used instead of the capillary.

In addition, the freezer unit may be provided below the main body and the refrigerator unit may be provided above the main body.

As illustrated in FIG. 2, the refrigerator further includes a user interface unit 140 provided in any of the two doors 131 and 132.

Here, the user interface unit 140 receives operation information of the refrigerator and displays the operation information of the refrigerator and food information of food stored in each storage container.

The user interface unit 140 receives a user's health information and examination time, displays the user's health information that is accumulated up to the present in order of the examination time, and may also display the user's health information for each period that is selected by the user.

The user interface unit 140 displays a recommended dish menu and prohibited food for each user.

Figure 3:
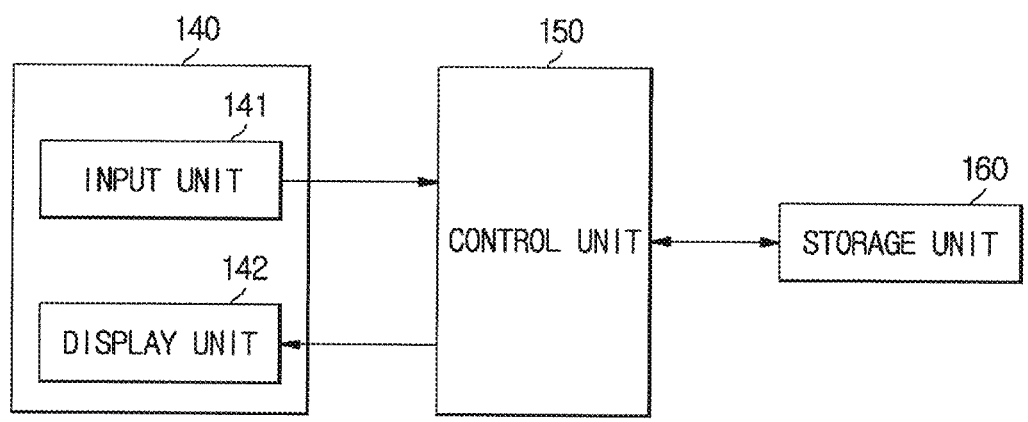
FIG. 3 illustrates a control configuration diagram of a refrigerator according to an embodiment.

As illustrated in FIG. 3, the refrigerator further includes a control unit 150 configured to control a freezing cycle based on operation information input to the user interface unit 140, and a target temperature and an interior temperature of each storage container, and a storage unit 160 configured to store the operation information. Details thereof will be described below.

The user interface unit 140 includes an input unit 141 configured to receive operation information from the user and a display unit 142 configured to display operation information of the refrigerator and information on food stored in each storage container.

Here, the input unit 141 may be implemented by a key, a button, and the like, and the display unit 142 may be implemented by an LCD and the like.

In addition, the input unit 141 and the display unit 142 may be implemented by a touch screen in which an image is displayed, and when a hand contacts a displayed text or picture, a location thereof is delivered as input information, and the image is changed to an image corresponding to the delivered input information and displayed.

That is, the input unit 141 may receive information by a method of drag or click.

The input unit 141 receives the user's user information and the user's health information. In this embodiment, the input unit 141 may also receive an examination time of currently received health information.

For example, the user information includes the user's name, ID, sex, age, and the like.

The health information includes at least one of a height, a body weight, a history, a blood pressure, a pulse, a blood glucose level, a body fat percentage, an electrocardiogram, a body temperature, an oxygen saturation level, a cholesterol level, and a stress level.

The examination time includes year, month, date, and time information and may further include minute and second information.

The input unit 141 may also receive an examination period when the health information is identified.

The input unit 141 receives food information of food to be stored in the storage container and may also receive selection of any recommended dish of the recommended dish menu.

Here, the food information includes a food name, an expiration date, and the like.

The input unit 141 receives a storage location of food to be stored in the storage container.

The input unit 141 receives food to be purchased from a wish list.

The input unit 141 may also receive information on food removed from the storage container.

The display unit 142 displays the user's health information in order of the examination time.

In addition, the display unit 142 may display health information within the examination period selected by the user and also display a time of the next health examination.

The display unit 142 displays food information of food stored in the storage container, the recommended dish menu, the prohibited food, the recommended food, the wish list, and the like. Accordingly, it is possible to increase utility and convenience for the user.

When information on food stored in the storage container is displayed, the display unit 142 displays a minimized internal structure of the actual refrigerator and may emphasize a design element by also displaying the food stored in the storage container.

The display unit 142 may display a location of an empty space of the storage container and also display an appropriate location of food to be stored.

The control unit 150 controls operations of the compressor, the first fan, the second fan, and the expansion valve based on the operation information, and the target temperature and the interior temperature of the storage container.

The control unit 150 controls storage of the user information, the health information, and the examination time input to the input unit. When a health care command is input to the input unit, the control unit 150 performs control such that health information of the user who requests the health care command is identified in order of the examination time and displayed on the display unit 142.

The control unit 150 performs control such that, when the examination period is input, health information within the input examination period is identified and displayed on the display unit 142.

The control unit 150 compares health information in order of the examination time, determines changes in the health state, generates a recommended dish menu based on the determined health state, health information, and information on food stored in the storage unit, compares food materials used for each recommended dish of the generated recommended dish menu with food stored in the storage container, identifies food that is not stored in the storage container, and adds the identified food to the wish list.

The control unit 150 controls display of food to be purchased for each dish when display of the wish list is controlled.

The control unit 150 determines a display priority based on an expiration date of food used as food materials for each dish when display of the recommended dish menu is controlled.

That is, the control unit 150 displays a recommended dish using food having an imminent expiration date as food materials with the highest priority and a recommended dish using food having the longest expiration date as food materials with the lowest priority.

The control unit 150 determines prohibited food based on the determined health state, the health information, and the information on food stored in the storage unit, and controls display of the determined prohibited food.

The control unit 150 controls storage of the storage location and food information input to the input unit.

When deletion of information on removed food is input, the control unit 150 updates information on food stored in the storage unit 160.

The control unit 150 may predict a next examination time based on an analyzed health state and control display of the predicted next examination time.

The storage unit 160 stores user information, and accumulates and stores health information input to the input unit for each user.

That is, the storage unit 160 stores all pieces of information including health information initially input to health care of the user interface unit and currently input health information. In addition, the health information stored in the storage unit 160 may be deleted by the user.

The storage unit 160 matches and stores the health information and the examination time for each user.

In addition, the examination time may be replaced with an input time at which the health information is input and stored.

The storage unit 160 stores food information and the storage location of food stored in the storage container 120.

The storage unit 160 stores a dish name that may be cooked using at least one article of food and recipe information for each dish.

The storage unit 160 stores food materials used for each dish and stores prohibited food for each disease.

An input/output example of the user interface unit 140 including the input unit and the display unit in this manner will be described with reference to FIGS. 4 to 12.

Figure 4:
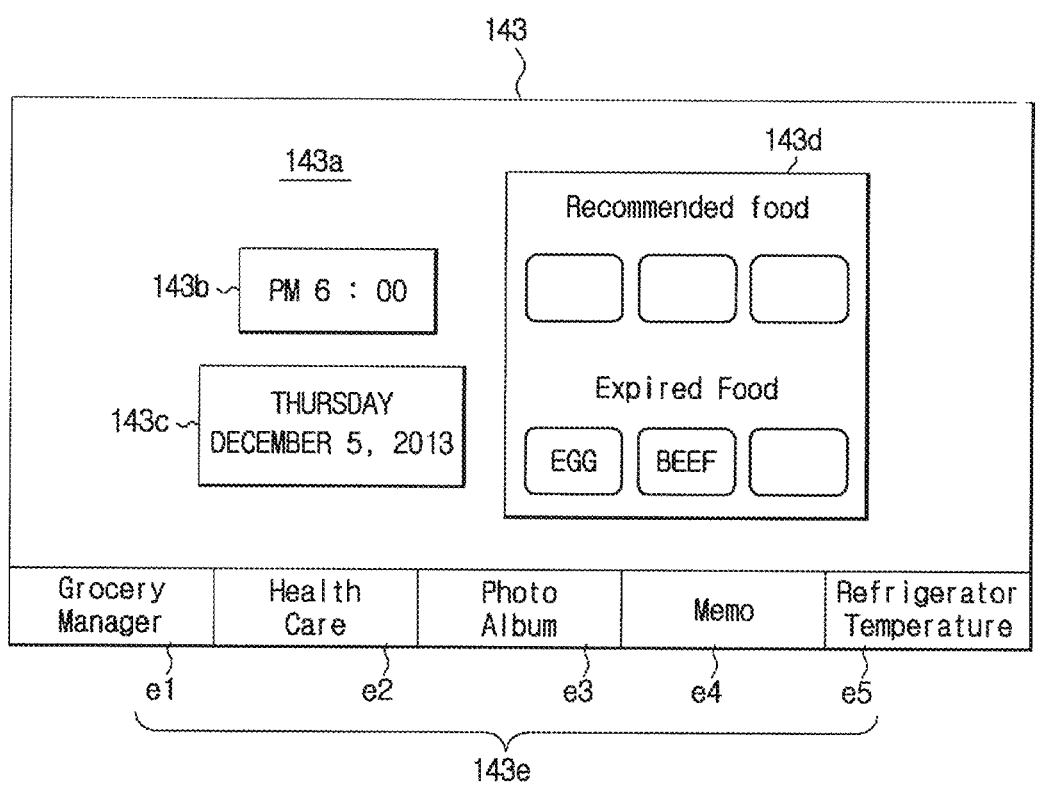
FIG. 4 illustrates an example of a default screen of a user interface unit included in a refrigerator according to an embodiment.

As illustrated in FIG. 4, a screen configuration of the user interface unit 140: 143 includes a background 143a, a clock window 143b, a calendar window 143c, a recommended food display window 143d, and a menu window 143e.

The background 143a displays a predetermined image. Here, examples of the predetermined image may include an image for each season or an image for each time interval (such as day and night).

The clock window 143b informs a user of the current time. Display of the current time may include, for example, display of a 24-hour clock or a 12-hour clock.

The calendar window 143c displays today's date or an image of this month's calendar.

The recommended food display window 143d displays recommended food that is recommend to be consumed soon due to an imminent expiration date and food which has expired.

When food is displayed on the recommended food display window 143d, the food is displayed in order from the most imminent expiration date and three images of food items whose expiration dates have passed in order from the oldest to the most recent.

A menu window 143e displays button images of a grocery manager e1, health care e2, a photo album e3 in which a photo related to a dish menu and the user's photo are stored, a memo e4 for inputting text, and a temperature e5 for setting the target temperature of the storage container.

Figure 5:
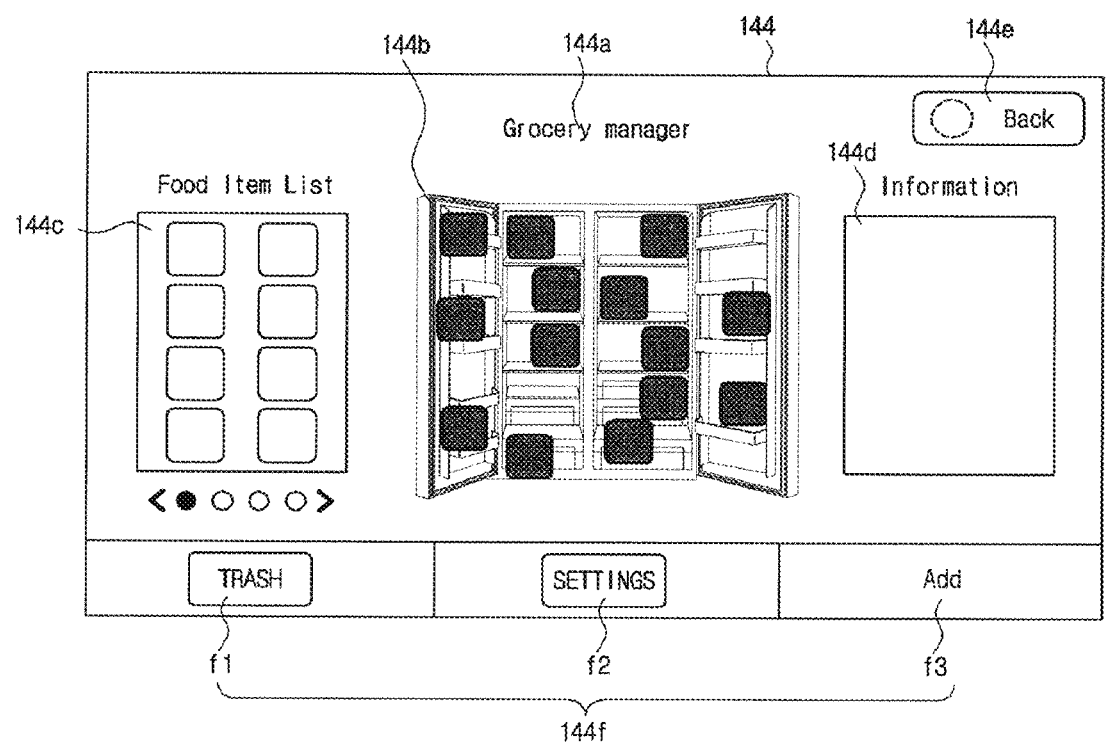
FIG. 5 illustrates an example of a grocery mode screen of a user interface unit included in a refrigerator according to an embodiment.

FIG. 5 is a diagram of an example grocery manager e1 that is displayed on the user interface unit 140: 144.

When a currently selected mode is a grocery manager mode, the user interface unit 140: 144 includes a background 144a of the grocery manager that displays a title of the grocery manager, an inside image window 144b that is disposed on the background 144a of the grocery manager at a center and has the same image as an internal structure of the main body, a food item list 144c that is disposed at a side of the inside image window 144b and has a plurality of food items, an information window 144d that is disposed at the other side of the inside image window 144b and receives usage information of food or outputs usage information, a back button 144e for switching to a previous screen, and a menu bar 144f for managing the grocery manager.

The inside image window 144b has areas corresponding to inside structures of the refrigerator unit and the freezer unit and receptacles of a door of the refrigerator unit and a door of the freezer unit, and displays food information of food stored in each location of each area.

Here, the inside image window 144b may be changed to show an image that is the same as an actual internal structure in response to an addition or deletion of the shelf.

The menu bar 144f includes a trash button f1 for deleting information on removed food, a setting button f2 used for settings desired by the user in a method of showing food items, and an add button f3 for adding information on food to be stored.

Figure 6:
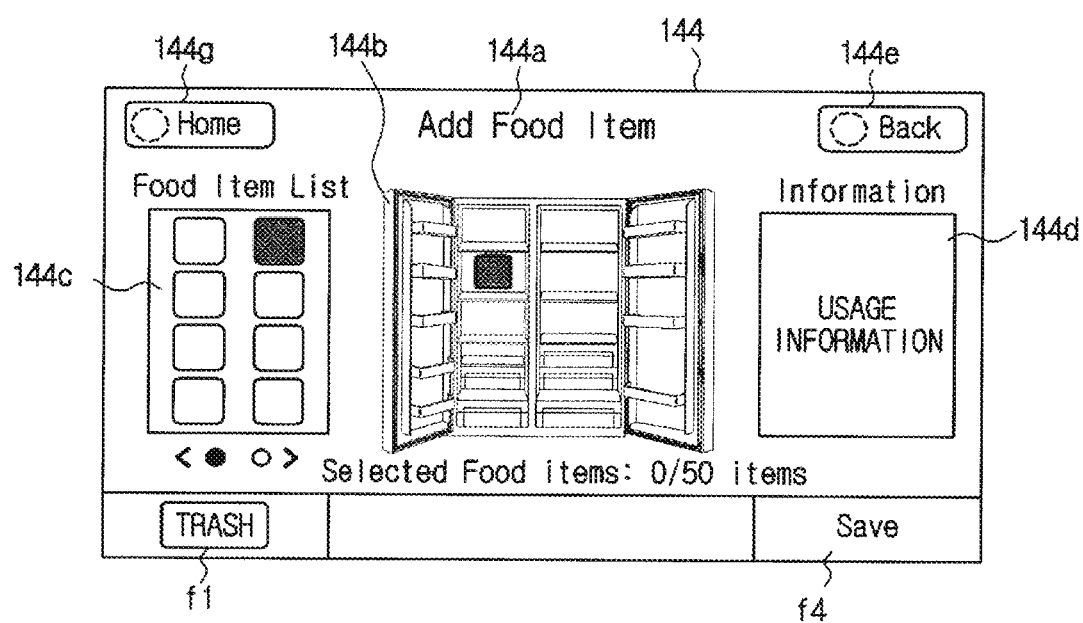
FIG. 6 illustrates an example of food location identification in a grocery mode of a user interface unit included in a refrigerator according to an embodiment.

FIG. 6 illustrates a diagram of an example food storage location display of the grocery manager e1.

As illustrated in FIG. 6, the food item list 144c displays food items in order from the oldest to the most recent storage date.

The food items displayed in the food item list 144c includes a food item, a date that is passed or remaining from a fresh storage date, or information on a storage date.

Also, the food item may be displayed in red when the fresh storage date has passed, yellow when the current day is the last day of the fresh period, and blue when the fresh period has not passed.

Also, when the food item of the food item list 144c is selected, the user interface unit 140: 144 highlights the food item of the food item list 144c and the food storage location in the inside image window 144b.

In addition, the food item list 144c of the user interface unit further includes a page section. The number of all circular buttons represents the number of pages in total. Among all circle buttons, a location of a filled-in circular button represents a current page.

FIGS. 7A-7D illustrate diagrams of example settings of food information and the storage location of food in a mode of the grocery manager e1.

Figure 7A:
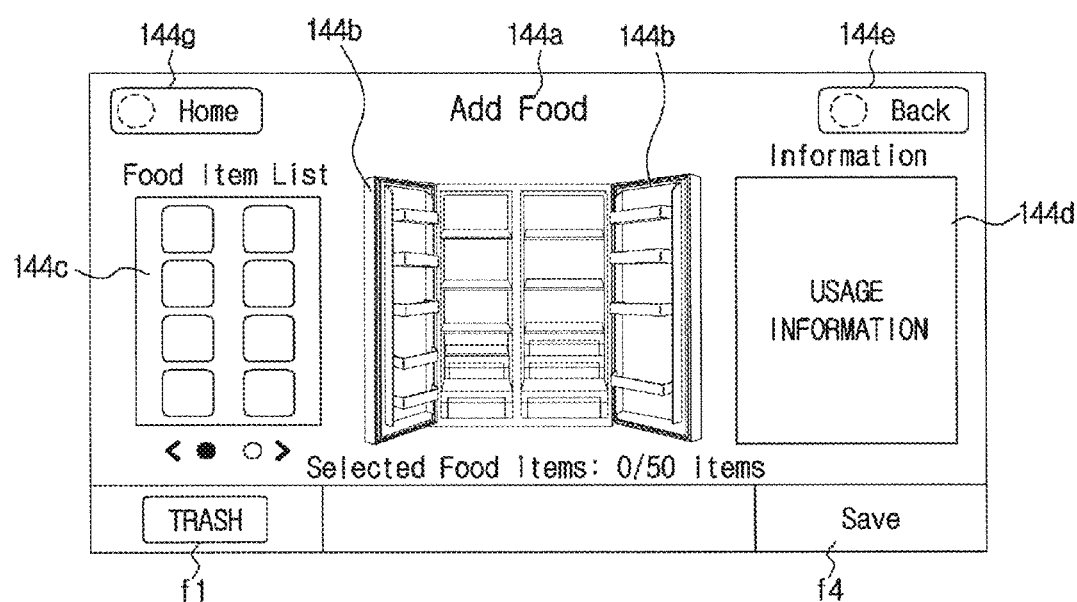
FIGS. 7A-7D illustrate examples of an addition of food to be stored in a storage container in a grocery mode of a user interface unit included in a refrigerator according to an embodiment.

As illustrated in FIG. 7A, when the grocery manager e1 is selected, the user interface unit 140: 144 displays the background 144a, the inside image window 144b, the food item list 144c, the information window 144d, the back button 144e, and the menu bar 144f.

Figure 7B:
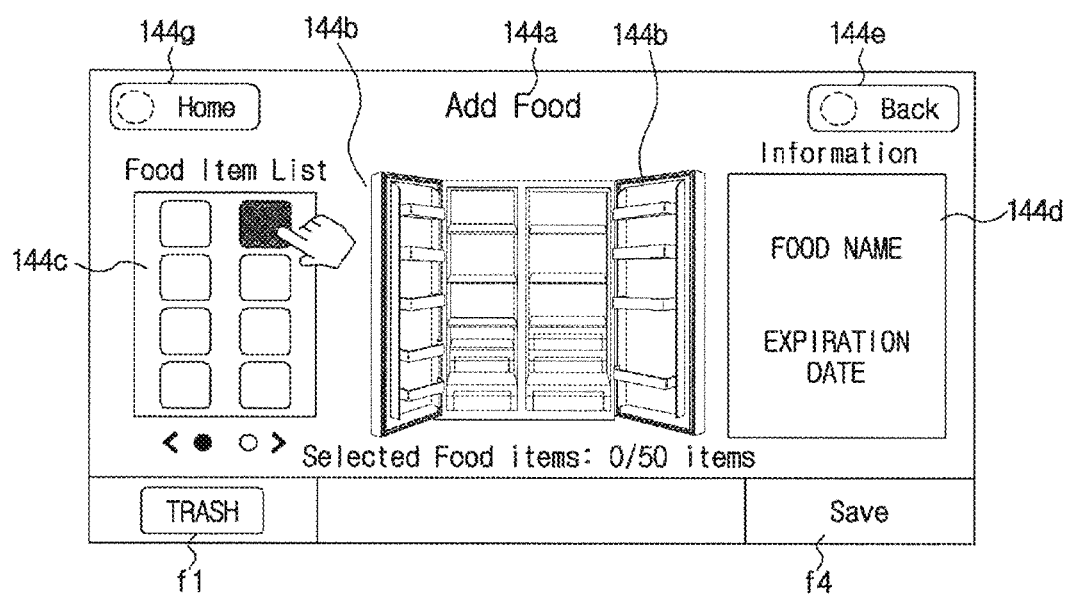

As illustrated in FIG. 7B, when the food item of the food item list 144c is selected, the user interface unit 140: 144 displays food information of a corresponding food item on the information window 144d.

Figure 7C:
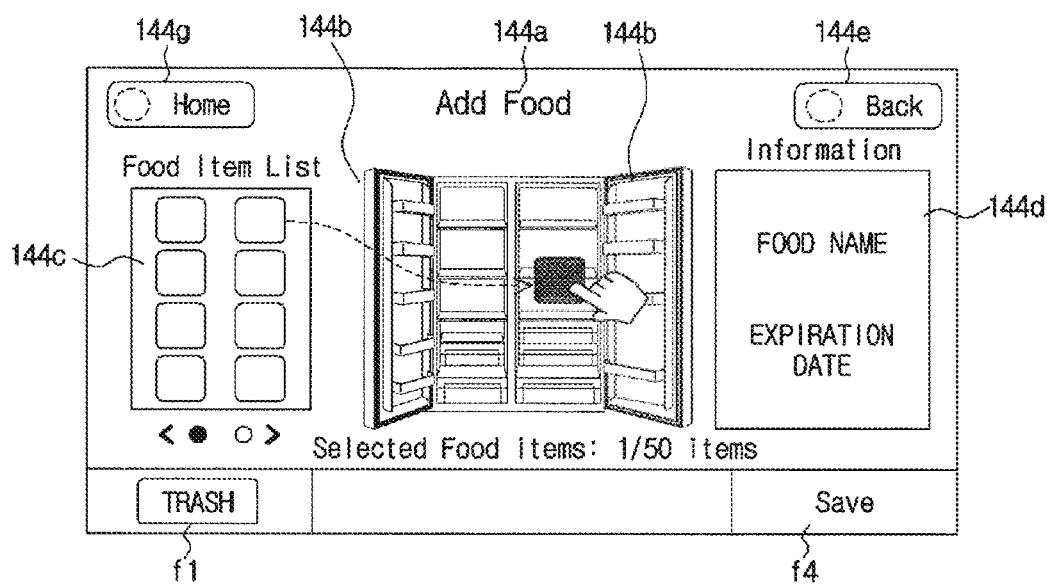

As illustrated in FIG. 7C, when the food item of the food item list 144c moves to any location in the inside image window 144b using a method of Drag & Drop and a save button is input, the user interface unit 140: 144 highlights a storage location of food in the inside image window 144b and stores the moved location as the storage location.

In addition, when the storage location of food is set, it is also possible to receive a recommendation of the storage location based on the food item.

Figure 7D:
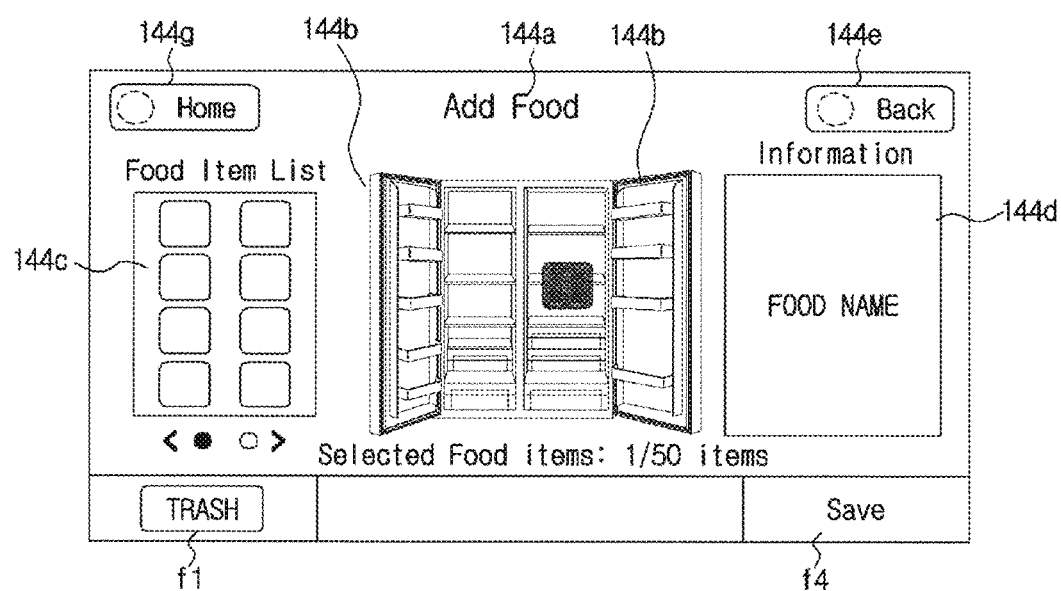

As illustrated in FIG. 7D, the user interface unit 140: 144 manipulates information displayed on the information window 144d, inputs food information corresponding to the food item, and stores the input food information and the storage location in the storage unit 160.

FIGS. 8A-8D illustrate diagrams of an example food removal by the grocery manager e1.

Figure 8A:
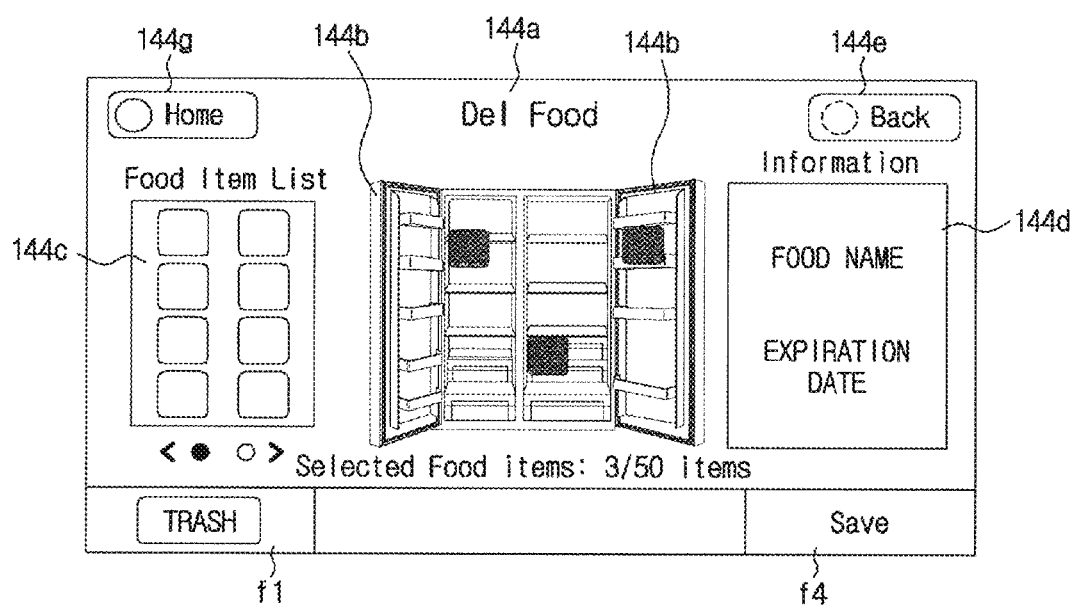
FIGS. 8A-8D illustrate examples of deleting food stored in a storage container in a grocery mode of a user interface unit included in a refrigerator according to an embodiment.

As illustrated in FIG. 8A, when the grocery manager e1 is selected, the user interface unit 140: 144 displays the background 144a, the inside image window 144b on which the storage location of food is displayed, the food item list 144c, the information window 144d, the back button 144e, and the menu bar 144f.

Figure 8B:
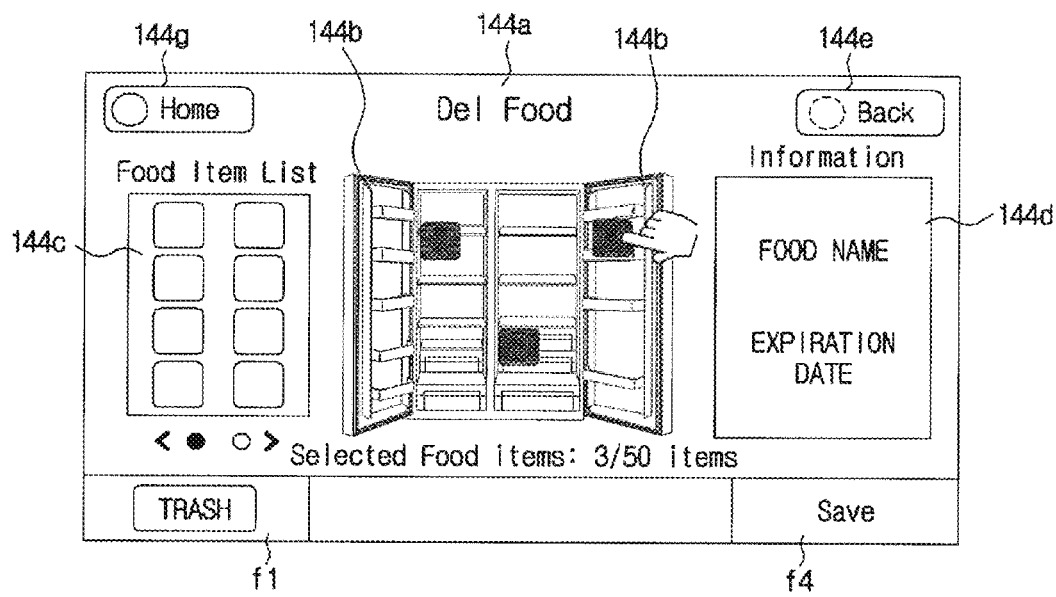

As illustrated in FIG. 8B, when a food item of food to be removed from among at least one food item in the inside image window 144b is selected, the user interface unit 140: 144 displays food information of food corresponding to the selected food item on the information window 144d.

Figure 8C:
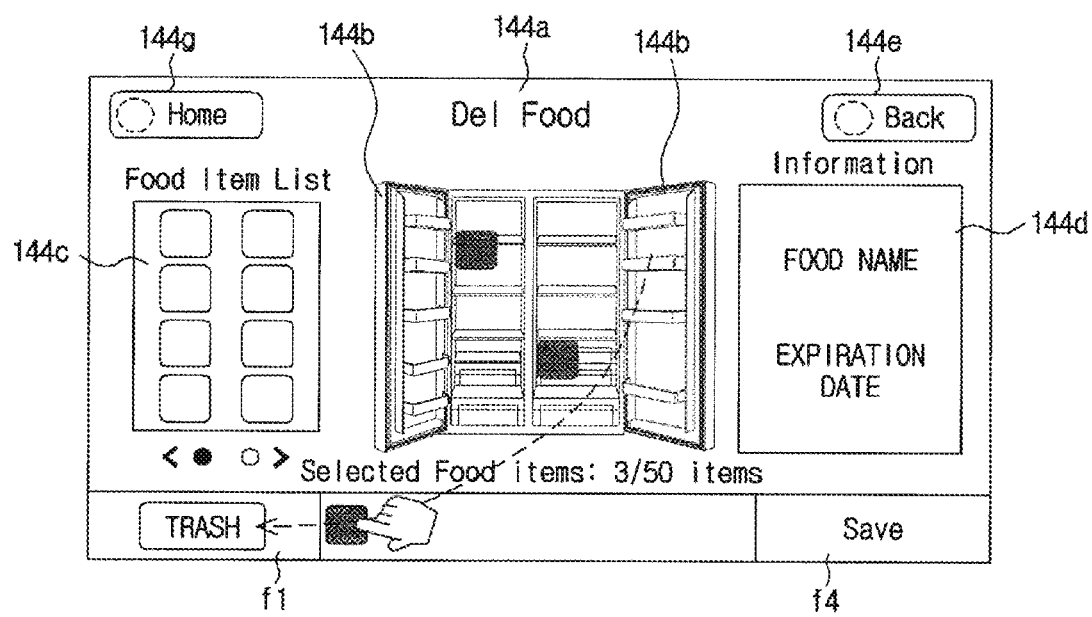
Figure 8D:
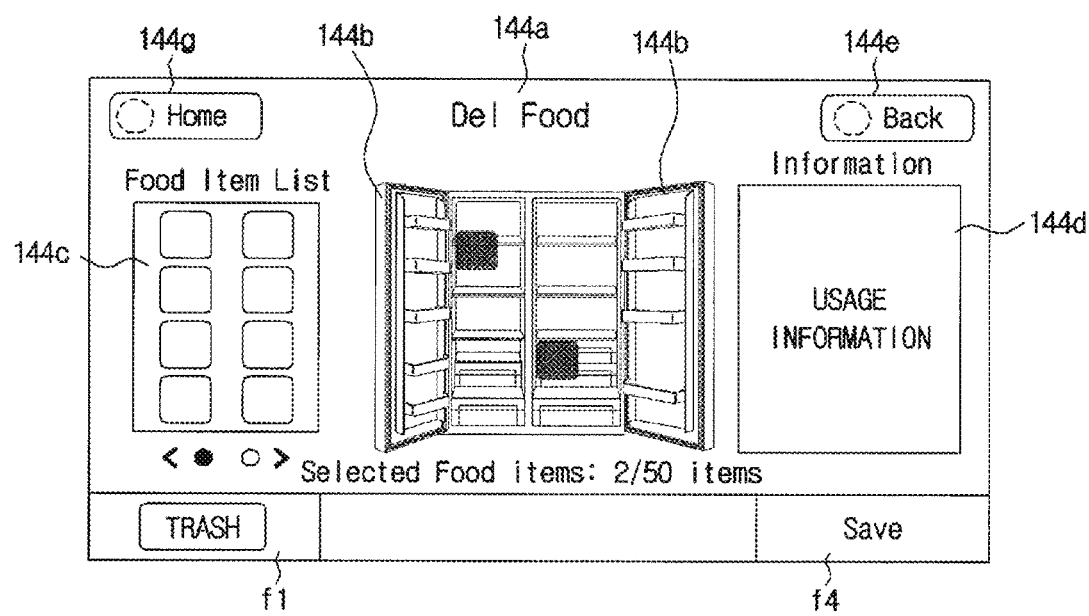

As illustrated in FIGS. 8C and 8D, when a food item of any location in the inside image window 144b is moved to the trash f1 using a method of Drag & Drop and a save button f4 is input, the user interface unit 140: 144 deletes a corresponding food item in the inside image window 144b.

In this embodiment, the refrigerator deletes the storage location and food information corresponding to the food item moved to the trash f1 from the storage unit 160.

In addition, when the storage location of the food item is set or deleted, if a dragging point is outside the food item list or the trash while the food item is being dragged, the user interface unit 140: 144 changes a color of the food item to gray to indicate inactivation.

Figure 9:
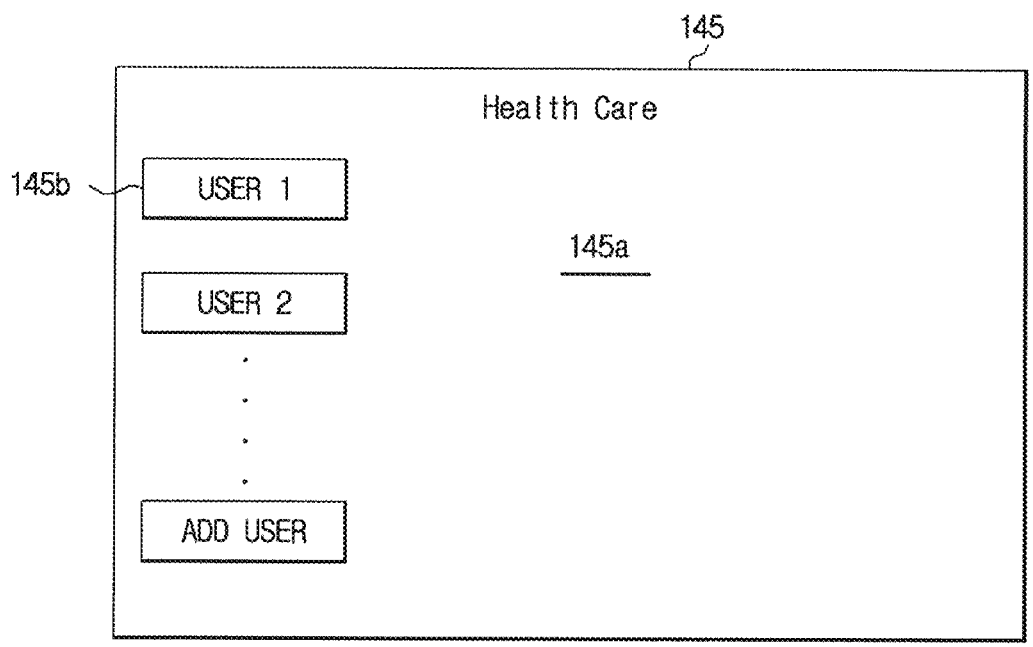
FIGS. 9 and 10 illustrate display examples of a health care mode screen of a user interface unit included in a refrigerator according to an embodiment.
Figure 10:
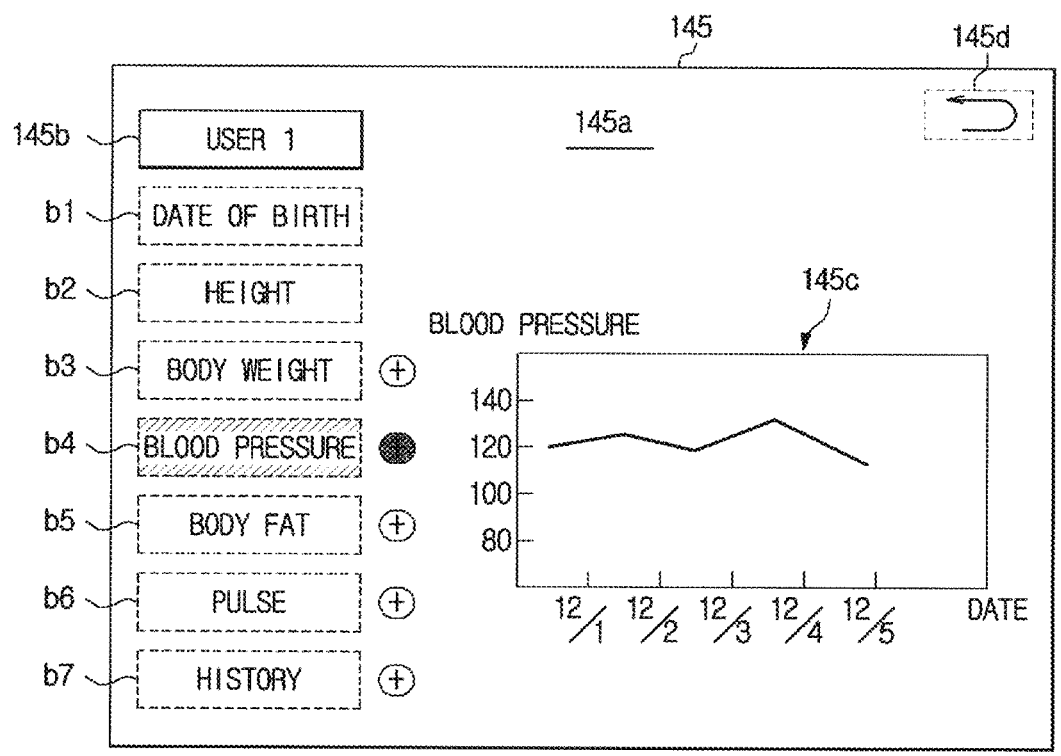

FIGS. 9 and 10 illustrate example display diagrams of a health care mode.

As illustrated in FIG. 9, when a currently selected mode is a health care mode, the user interface unit 140: 145 displays a health care background 145a for displaying a title of a health mode and an ID button 145b for displaying an ID that is user information of a pre-registered user, and further displays a user add button for adding a non-registered user.

As illustrated in FIG. 10, when any user is selected from among a plurality of users, the user interface unit 140: 145 displays the user information 145b of the selected user and at least one examination item.

Here, the examination item is displayed in the form of a button in order to receive a command for displaying accumulated health information.

That is, the user interface unit 140: 145 further includes examination item buttons b1 to b7.

In addition, the examination item may be set by the user.

When any examination item button among examination items is touched, the user interface unit 140: 145 displays health information about the touched examination item button on a health information window 145c in order of the examination time and may further display a back button 145d for returning to a previous screen (a screen of FIG. 9).

Here, display of the health information in order of the examination time may include display in the form of a table and display in the form of a graph.

In addition, the health information may be displayed on an empty area in the background 145a of a current screen.

The user interface unit 140: 145 includes an additional input button (+) for each examination item. When any additional input button (+) is touched, an input window capable of additionally inputting health information of a corresponding examination item is displayed.

Here, the input window includes a health information input window 145e for inputting examined health information and an examination time input window 145f for inputting an examination date and time.

Figure 11:
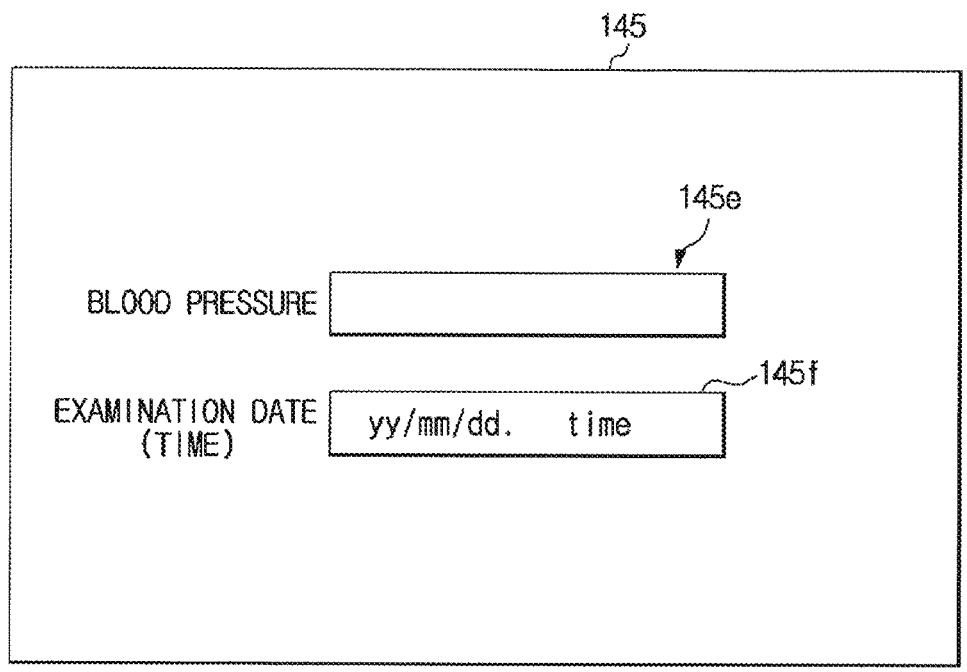
FIG. 11 illustrates an example of health information in a health care mode screen of a user interface unit included in a refrigerator according to an embodiment.

As illustrated in FIG. 11, after the current screen is switched, the user interface unit may also display the input windows 145e and 145f on the switched screen.

Figure 12:
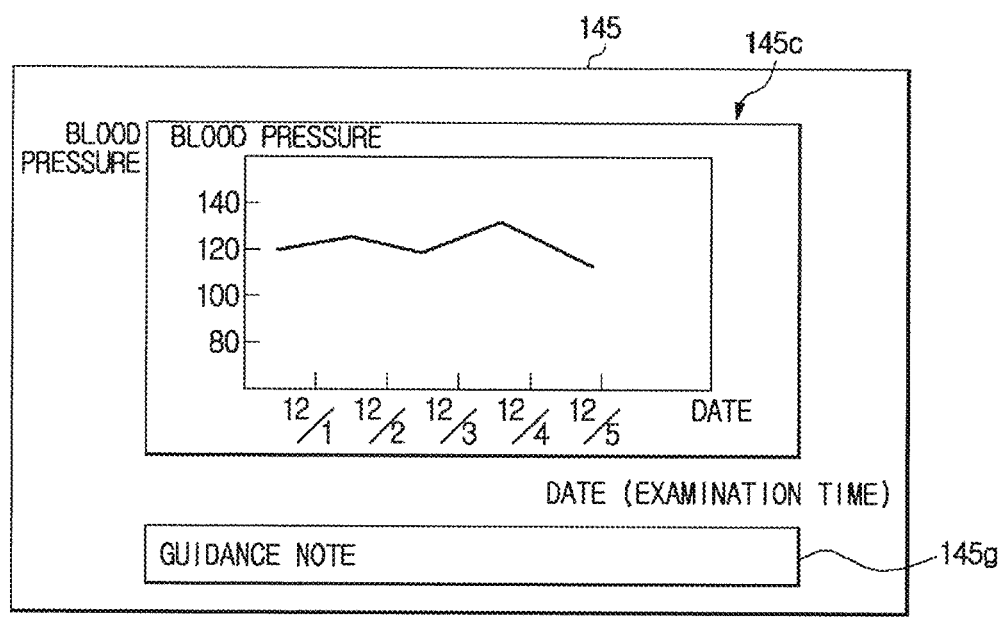
FIG. 12 illustrates an input window display example of health information of a health care mode screen of a user interface unit included in a refrigerator according to an embodiment.

In an embodiment, as illustrated in FIG. 12, when the health information window 145c is displayed, the user interface unit 145 may switch a screen and display a graph on an entire area of the switched screen. In this embodiment, the user interface unit may also display a change in the health state corresponding to a change of the examination time as a guidance note 145g.

Figure 13:
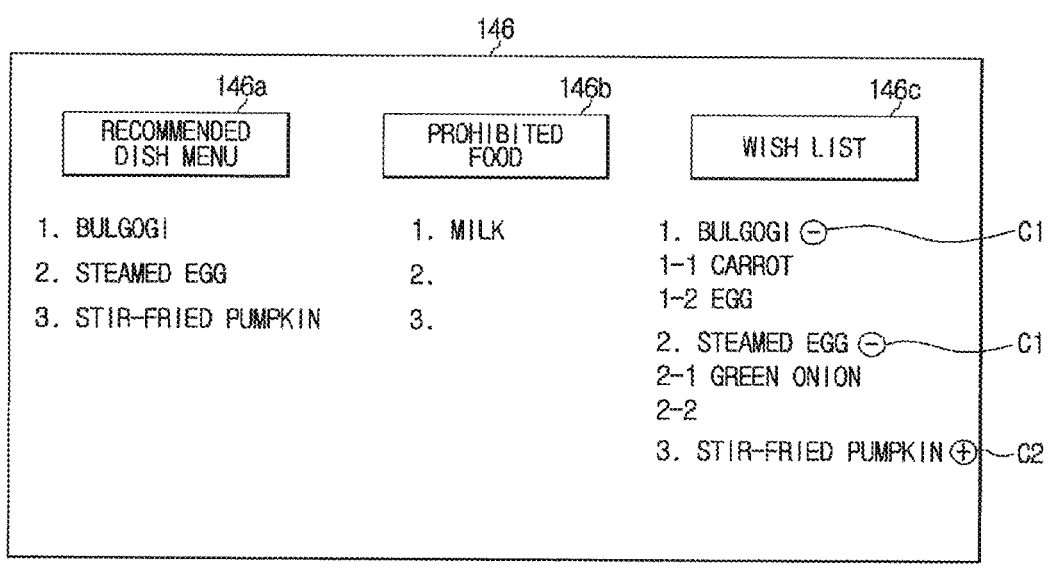
FIG. 13 illustrates an example of a service item in a health care mode screen of a user interface unit included in a refrigerator according to an embodiment.
Figure 14:
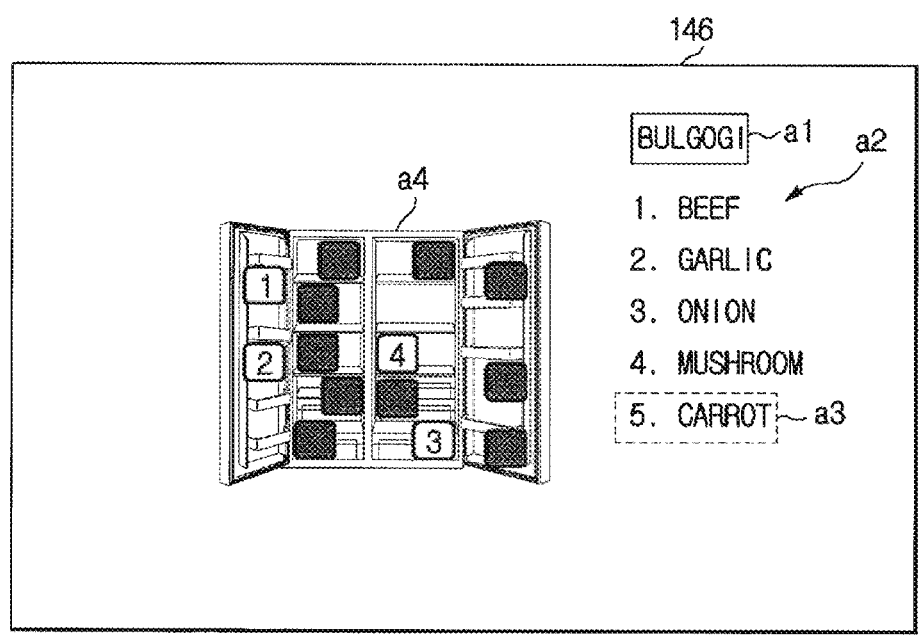
FIG. 14 illustrates an example of a recommended dish selection in a health care mode screen of a user interface unit included in a refrigerator according to an embodiment.

FIGS. 13 and 14 illustrate diagrams of example service items for health promotion generated based on the food information and health information stored in the storage unit.

As illustrated in FIG. 13, the user interface unit 140: 146 displays a recommended dish menu 146a based on the user's health information, prohibited food 146b which the user abstains from consuming, and a wish list 146c for displaying food that is not stored in the storage container among food materials used for a dish of the recommended dish menu.

Here, a recommended dish of the recommended dish menu includes at least one dish, prohibited food also includes at least one food, and food of the wish list displays food necessary for each recommended dish.

As illustrated in FIG. 14, when any recommended dish is selected from the recommended dish menu, the user interface unit 140: 146 displays a dish name a1 of the selected recommended dish, a food name a2 of a food material that is stored in the storage container among food materials used for the recommended dish, a name of food a3 that is not stored in the storage container and is recommend to be purchased, and an inside image window a4 for displaying the storage location of food materials stored in the storage container.

That is, when the storage location is displayed on the inside image window a4, the refrigerator performs display based on the storage location for each food stored in the storage unit.

Figure 15:
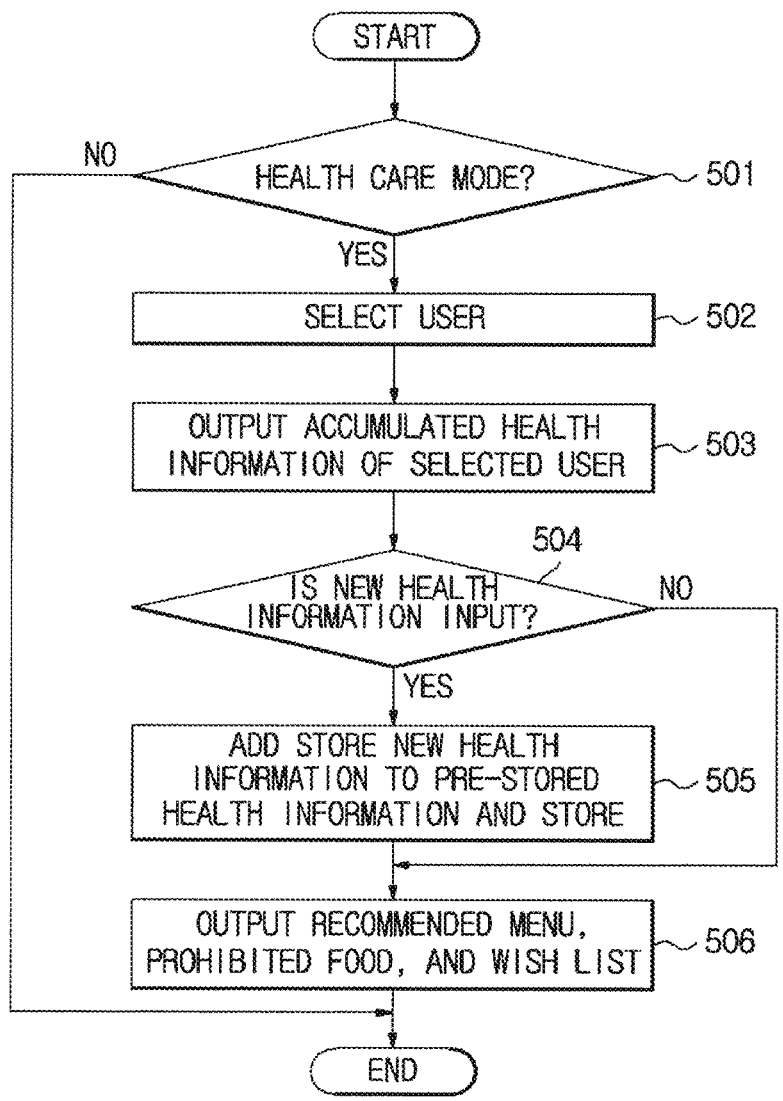
FIG. 15 illustrates a control process of a refrigerator according to an embodiment.

FIG. 15 illustrates a process of controlling a refrigerator according to an embodiment.

The refrigerator operates the compressor when power is applied from an external commercial power source, selectively rotates the first fan and the second fan to cool the freezer unit serving as the first storage container and the refrigerator unit serving as the second storage container, and keeps food stored therein fresh.

In this embodiment, information on food stored in each storage container is previously stored in the storage container.

Here, the information on food includes a food name, information on food having an expiration date, and information on the storage location of food. Management of such food may be performed by the method illustrated in FIGS. 5 to 8.

The user interface unit of the refrigerator maintains a waiting state and determines whether a command for switching to the health care mode is input (501).

When the user touches a health care button e2 of the menu window 143e, a mode enters the health care mode.

The refrigerator switches a current mode to the health care mode and displays user information of a pre-registered user for performing the health care mode (refer to FIG. 9).

Here, display of the user information includes display of the user's name or ID in the form of a button.

The refrigerator receives selection of any user among the pre-registered users (502).

That is, when any button on which user information is displayed among the pre-registered users is touched, the refrigerator identifies user information of the touched location.

Here, while a method of touching the button on which user information is displayed has been exemplified as a method of receiving the user information, the user information may also be received using biometrics such as fingerprint recognition.

Then, the refrigerator displays the examination item and user information of the selected user (refer to FIG. 10).

Here, the user information includes information on a name, an ID, a date of birth, and the like, and the examination item may be set by the user.

Then, when the user touches any examination item button, the refrigerator extracts and outputs accumulated health information of the touched examination item (503).

When the examination item is, for example, a blood pressure, the user interface unit 140 displays blood pressures from an initially input blood pressure to a most recently input blood pressure in order of the examination time.

Then, when the user touches the additional input button (+) displayed at a side of any examination item among a plurality of examination items, the refrigerator displays the health information input window 145e for inputting new health information of the touched examination item and the examination time input window 145f for inputting an examination date and time (refer to FIG. 11).

While outputting only health information of one examination item has been exemplified in this embodiment, health information of the plurality of examination items may also be output.

Then, when the user inputs the health information and the examination time (504), the refrigerator adds and stores currently input health information to previously accumulated and stored health information (505). In this embodiment, the storage unit 160 matches, accumulates, and then stores the health information and the examination time.

In an embodiment, when health information is input, if the examination time is not input, an input time at which health information is input may also be replaced with the examination time and stored.

Then, the refrigerator displays health information of accumulated and stored examination items in order of the examination time.

In addition, when the examination period is selected by the user, the refrigerator may also extract and display health information within the selected examination period. In this embodiment, health information of the selected examination item is displayed.

For example, when the examination period has a start date of Jan. 1, 2013 and an end date of Dec. 30, 2013, health information examined from Jan. 1, 2013 to Dec. 30, 2013 is extracted and displayed.

Then, the refrigerator analyzes the accumulated and stored health information, determines his or her health state, and provides notification information of the determined health state as a guidance note.

For example, the refrigerator displays the user's health information about the examination item in the form of a graph in order of the examination time and displays notification information about the health state as a guidance note (refer to FIG. 12).

Examples of the guidance note include "Please be careful of an increase in blood pressure since hypertension may occur," and "Please eat low calorie food for a week since there is a risk of an increase in body fat percentage."

Then, the refrigerator analyzes the accumulated and stored health information, determines his or her health state, and provides a service for the user's health promotion based on the determined health state. In this embodiment, when there is a plurality of examination items, the accumulated and stored health information is extracted for each of the plurality of examination items and various pieces of health information are comprehensively analyzed.

That is, the refrigerator generates and displays the recommended dish menu made of food that is good for the user to eat based on the accumulated and stored health information and information on food stored in the storage container, and identifies and displays prohibited food that is not good for the user to eat based on the accumulated and stored health information and information on food stored in the storage container (refer to FIG. 13).

When the expiration date of the food is not indicated, the expiration date may be set to a time at which a predetermined time has passed from a purchase date. In addition, the refrigerator provides a predetermined lifetime for each food in order to set the expiration date according to the user's request.

Here, when the recommended dish menu is generated, the menu is generated based on an expiration date of food used for the dish, and a dish using food having an imminent expiration date is set to have a high display priority.

In addition, a dish made of food that helps health promotion when the user eats the food may also be displayed to have top priority.

In an embodiment, the refrigerator determines food that is harmless to health when the user eats the food or food that helps health promotion when the user eats the food among food stored in the storage container based on the user's health information, history, and health state, and determines a dish that may be made of the determined food.

Here, determination of the dish that may be made of the determined food includes identifying a food material list for each dish stored in the storage unit 160 and determining a dish in which the determined food is included as a food material.

In addition, food stored in the storage container 120 is based on food information stored in the storage unit 160.

In an embodiment, when the recommended dish is generated, if food materials used for the recommended dish include both the recommended food and the prohibited food, the refrigerator excludes the dish from the recommended dish menu.

The refrigerator generates and displays the determined dish as the recommended dish menu.

In an embodiment, the refrigerator identifies each expiration date of the determined food, determines a usage priority of food in order from the most imminent expiration date, and determines a display priority of the recommended dish based on the determined usage priority of the food.

For example, when the recommended dish menu includes bulgogi, steamed eggs, and stir-fried pumpkin, and an expiration date of beef is in 1 day, an expiration date of eggs is in 2 days, an expiration date of pumpkin is in 3 days, a usage priority of the beef is set to 1, a usage priority of the eggs is set to 2, and a usage priority of the pumpkin is set to 3. Therefore, bulgogi that is a recommended dish using the beef has a first display priority, the steamed eggs that is a recommended dish using the eggs has a second display priority, and the stir-fried pumpkin using the pumpkin has a third display priority.

That is, the user interface unit of the refrigerator displays bulgogi as the first recommended dish, the steamed eggs as the second recommended dish, and the stir-fried pumpkin as the third recommended dish.

In addition, according to a type of food stored in the refrigerator, the recommended dish menu may include one recommended dish.

In an embodiment, the refrigerator adds food to a wish list and displays the food that is food made of a food material that is not stored in the storage container among food materials necessary for cooking a dish of the recommended dish menu and is recommend to be purchased (506).

For example, when it is determined that a carrot necessary for cooking bulgogi among the recommended dish menu is not stored in the storage container, the carrot is added to the wish list.

In this embodiment, by displaying food that is recommend to be purchased for each dish in the wish list, the user may easily and wisely determine food that is recommend to be purchased.

That is, bulgogi that is a recommended dish name is displayed in the wish list, and an extend button (+: c1) is displayed at a side of the recommended dish name. When the extend button (+: c1) is touched, the button is changed to a shrink button (−: c2) and the carrot as food that is recommend to be purchased is displayed below the shrink button (−: c2).

In an embodiment, without display of the recommended dish, only the food that is recommend to be purchased may be displayed in the wish list.

In an embodiment, when the user selects bulgogi among the recommended dish menu, the refrigerator displays food materials necessary for cooking bulgogi and displays the food name a3 of food materials that are not stored in the storage container using a display method different from that of the food name a2 of food materials that are stored in the storage container.

Here, the display method may include a font, a color of text, or shading.

Then, the refrigerator displays a location of food of food materials stored in the storage container on the inside image window a4.

In this embodiment, the food name a2 of food materials stored in the storage container is numbered, and the same number is assigned to a corresponding location of the inside image window a4 corresponding to the storage location of the food stored in the storage container (refer to FIG. 14).

That is, the number 1 is assigned to beef, the number 2 is assigned to garlic, the number 3 is assigned to onions, and the number 4 is assigned to mushrooms, and the numbers are displayed. Among a plurality of locations of the inside image window, the number 1 is displayed in the storage location of the beef, the number 2 is displayed in the storage location of the garlic, the number 3 is displayed in the storage location of the onions, and the number 4 is displayed in the storage location of the mushrooms.

In an embodiment, the refrigerator determines a next examination time based on the user's health information, history, and health state, displays the determined examination time along with the examination item such that the user is informed of the next examination time. Also, the refrigerator informs the user again that a current day is the examination time through an alarm when the next examination time is reached.

Figure 16:
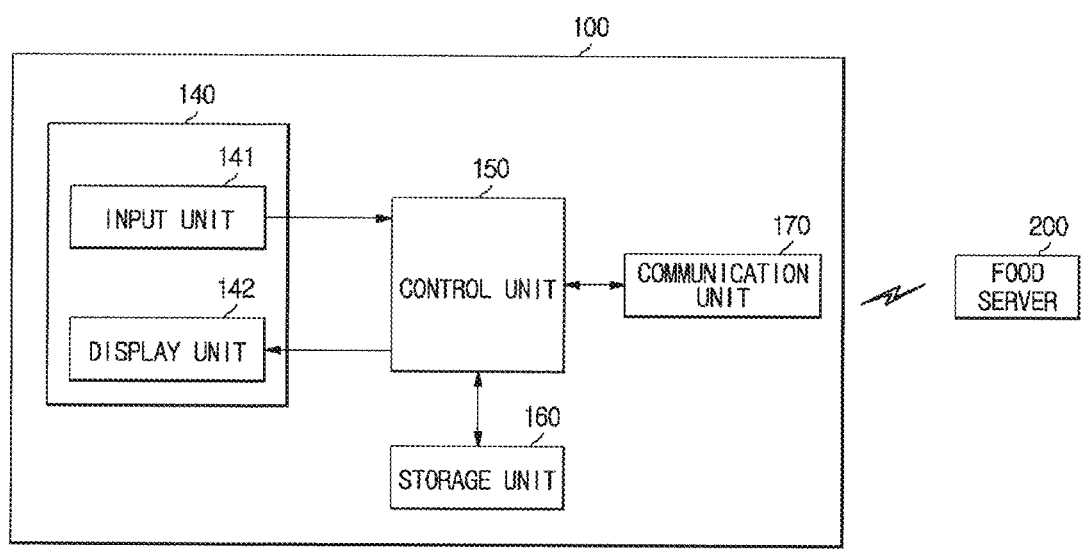
FIG. 16 is a control configuration diagram of a refrigerator according to another embodiment.

FIG. 16 illustrates a control configuration diagram of a refrigerator according to another embodiment.

Unlike the previous embodiment, a refrigerator according to another embodiment further includes a communication unit 170 configured to communicate with a food server 200.

The communication unit 170 may perform wired and/or wireless communication and perform communication with the external food server 200.

The communication unit 170 transmits at least one piece of food information selected by the user to the food server 200. In this embodiment, the communication unit 170 also transmits the user's user information.

Here, the food information includes information on a food name and a quantity, and the user information includes the user's address, the user's ID or name, and the like.

In addition, the communication unit 170 may also further transmit information on a delivery request date and time selected by the user.

The food server 200 is a server related to an Internet shopping mall selling food. When a food order request signal is received from the user, the food server 200 identifies a food list in the received food order request signal and instructs delivery of food in the identified food list to a corresponding Internet shopping mall.

Configurations of the user interface unit 140, the control unit 150, and the storage unit 160 that are the same as those in the previous embodiment will not be described. In other words, a configuration related to the communication unit 170 will be described.

Figure 17:
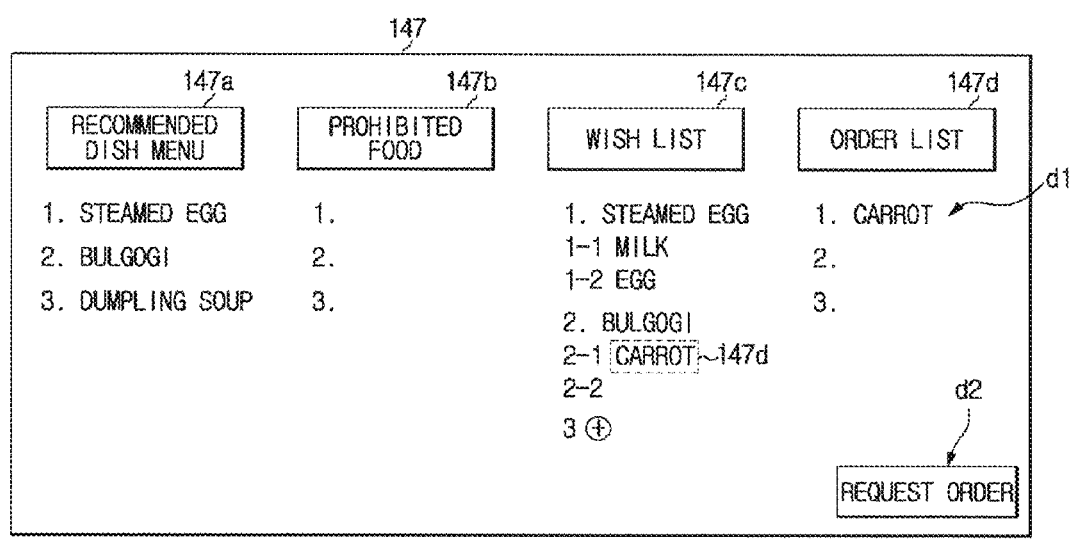
FIG. 17 illustrates an example of a user interface unit included in a refrigerator according to another embodiment.

As illustrated in FIG. 17, the user interface unit 140: 147 displays a recommended dish menu 147a based on the user's health information, prohibited food 147b which the user abstains from consuming, a wish list 147c for displaying food that is not stored in the storage container among food materials used for a dish of the recommended dish menu, and an order list 147d for displaying food that is food selected by the user among food in the wish list and determined to be purchased.

Here, a recommended dish of the recommended dish menu includes at least one dish, prohibited food also includes at least one food, and food of the wish list displays food necessary for each recommended dish.

The user interface unit 140 displays a food name d1 of food that is determined to be purchased as sub information of the order list 147d and displays an order request button d2 for requesting an order.

The control unit 150 adds food selected by the user among food in the wish list to the order list, and when the order request button d2 is input, transmits a food order request signal to the related food server 200.

When a delivery completion signal and food information of delivered food are received from the food server 200, the control unit 150 stores the received food information. When the storage location is input through the input unit of the user interface unit, the control unit 150 matches the food information and the storage location.

Also, the control unit 150 may recommend the storage location to the user based on the food information.

In addition, the control unit 150 may also directly receive the food information using the grocery manager in the input unit of the user interface unit.

The control unit 150 manages food and provides the accumulated health information to the user the same according to the previous embodiment.

The storage unit 160 matches and stores the received food information and input storage location.

Figure 18:
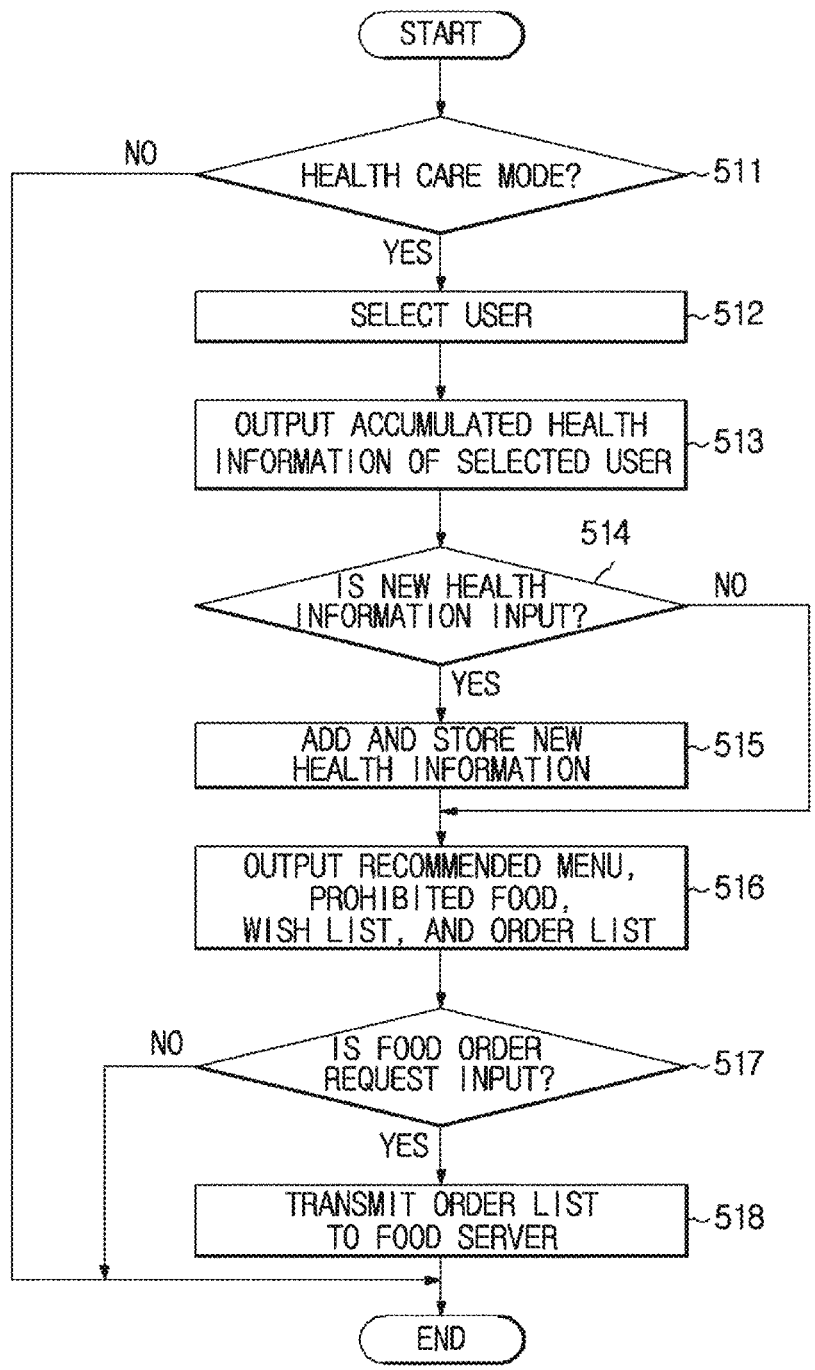
FIG. 18 illustrates a control process of a refrigerator according to another embodiment.

FIG. 18 illustrates a control process of a refrigerator according to another embodiment.

Configurations that are the same as those in the previous embodiment are briefly described.

The refrigerator controls the freezing cycle, keeps an interior temperature of the storage container at a target temperature, and therefore keeps food stored in each storage container fresh.

In this embodiment, information on food stored in each storage container is previously stored in the storage unit 160.

Here, the information on food includes a food name, information on food having an expiration date, and information on the storage location of food. Management of the food may be performed by the method illustrated in FIGS. 5 to 8.

Also, when food information of purchased food is received from the food server, the refrigerator stores the received food information in the storage unit.

The user interface unit of the refrigerator maintains a waiting state and determines whether the health care mode is input (511).

That is, when the user touches the health care button of the menu window of the user interface unit, a mode enters the health care mode.

The refrigerator switches a current mode to the health care mode and displays user information of a pre-registered user for performing the health care mode in this embodiment (refer to FIG. 9).

Here, display of the user information includes display of the user's name or ID in the form of a button.

The refrigerator receives selection of any user among the pre-registered users (512).

That is, when any button on which user information is displayed among the pre-registered users is touched, the refrigerator determines user information of the touched location.

Then, the refrigerator displays user information of the selected user and the examination item (refer to FIG. 10).

Then, when the user touches any examination item button, the refrigerator extracts and outputs accumulated health information of the touched examination item (513).

When the examination item is, for example, a blood pressure, the user interface unit 140 displays blood pressures from an initially input blood pressure to a most recently input blood pressure in order of the examination time.

Then, when the user touches the additional input button (+) displayed at a side of any examination item among a plurality of examination items, the refrigerator displays the health information input window 145e for inputting new health information of the touched examination item and the examination time input window 145f for inputting an examination date and time (refer to FIG. 11).

Then, when the user inputs the health information and the examination time (514), the refrigerator adds and stores currently input health information to previously accumulated and stored health information (515). In this embodiment, the storage unit 160 matches the health information and the examination time, and accumulates and stores.

Also, when health information is input, if the examination time is not input, an input time at which health information is input may also be replaced with the examination time and stored.

Then, the refrigerator displays health information of accumulated and stored examination items in order of the examination time.

In addition, when the examination period is selected by the user, the refrigerator may also extract and display health information within the selected examination period. In this embodiment, health information of the selected examination item is displayed.

Then, the refrigerator analyzes the accumulated and stored health information, determines his or her health state, and provides notification information of the determined health state as a guidance note.

For example, the refrigerator displays the user's health information about the examination item in the form of a graph in order of the examination time and displays notification information about the health state as a guidance note there below (refer to FIG. 12).

Then, the refrigerator analyzes the accumulated and stored health information, determines his or her health state, and provides a service for the user's health promotion based on the determined health state. In this embodiment, when there is a plurality of examination items, the accumulated and stored health information is extracted for each of the plurality of examination items and various pieces of health information are comprehensively analyzed.

That is, the refrigerator generates and displays the recommended dish menu made of food that is good for the user to eat based on the accumulated and stored health information and information on food stored in the storage container, and identifies and displays prohibited food that is not good for the user to eat based on the accumulated and stored health information and information on food stored in the storage container (refer to FIG. 13).

Here, when the recommended dish menu is generated, the menu is generated based on an expiration date of food used for the dish, and a dish using food having an imminent expiration date is set to have a high display priority.

Also, the refrigerator adds food to a wish list and displays the food that is food made of a food material that is not stored in the storage container among food materials necessary for cooking a dish of the recommended dish menu and is recommend to be purchased. Food selected by the user from among food in the wish list is recognized as food for an order and the recognized food is added to the order list and displayed (516).

For example, when it is determined that a carrot necessary for cooking bulgogi among the recommended dish menu is not stored in the storage container, the carrot is added to the wish list. When the carrot is selected in the wish list, the carrot is added to the order list.

Then, the refrigerator determines whether a food order request button is input. When it is determined that the food order request button is input (517), the refrigerator transmits a food order request signal to the food server 200. In this embodiment, food information of the order list and the user information are transmitted together (518).

After the order is completed, when food information of delivered food is received from the food server, the refrigerator stores the received food information.

Then, the refrigerator identifies a location of an empty space among an area of the storage container, determines a storage location that is appropriate to store the purchased food based on the received food information and the location of the empty space, displays the determined storage location through the user interface unit, and therefore the appropriate storage location of the purchased food may also be provided to the user.

In addition, when the user stores the purchased food in the storage container, if the food information and the recommended storage location are selected together, the selected storage location and the food information are matched and the matching storage location and food information are stored in the storage unit 160.

Also, the user may arbitrarily select the storage location of food

Figure 19:
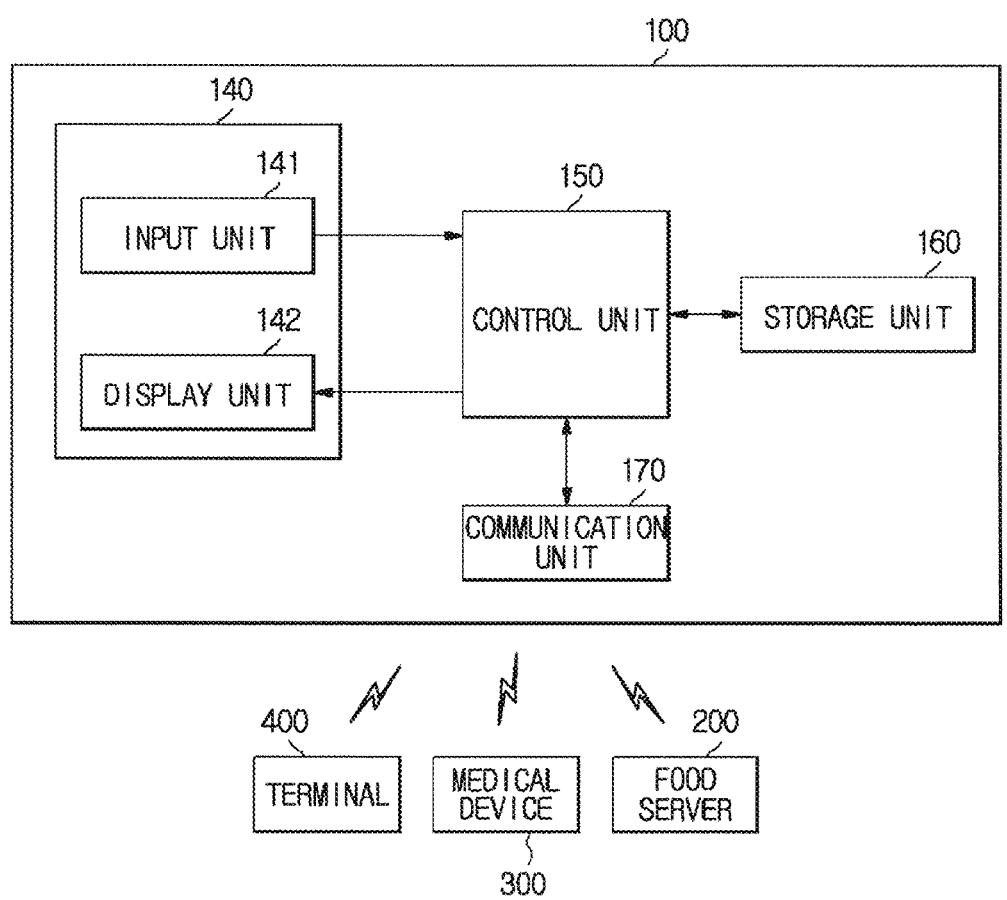
FIG. 19 illustrates a control configuration diagram of a refrigerator according to still another embodiment.

FIG. 19 illustrates a control configuration diagram of a refrigerator according to still another embodiment.

Unlike another embodiment, a refrigerator according to still another embodiment further includes the communication unit 170 configured to communicate with at least one external device among a medical device 300 and a terminal 400.

In addition, the communication unit 170 of the refrigerator according to still another embodiment also communicates with the food server 200.

The communication unit 170 performs wired and/or wireless communication, performs communication with the external food server 200, and communicates with at least one external device among the medical device 300 and the terminal 400.

The communication unit 170 transmits at least one piece of food information selected by the user to the food server 200. In this embodiment, the communication unit 170 also transmits the user's user information.

Here, the food information includes information on a food name and a quantity, and the user information includes the user's address, the user's ID or name, and the like.

In addition, the communication unit 170 may also further transmit information on a delivery request date and time selected by the user.

The communication unit 170 receives the user's health information and examination time from at least one external device among the medical device 300 and the terminal 400.

The communication unit 170 may also receive the user information.

The food server 200 is a server related to an Internet shopping mall selling food. When a food order request signal is received from the user, the food server 200 identifies a food list in the received food order request signal and instructs delivery of food in the identified food list to a corresponding Internet shopping mall.

The medical device 300 includes all devices capable of examining health states such as a blood pressure, a pulse, a body fat percentage, a blood glucose level, a body temperature, an electrocardiogram, a stress level, and the like. The terminal 400 is a device that may perform mobile communication and includes a smartphone, a tablet, a laptop computer, and the like.

Among examples of the terminal, the smartphone will be exemplified.

Figure 20:
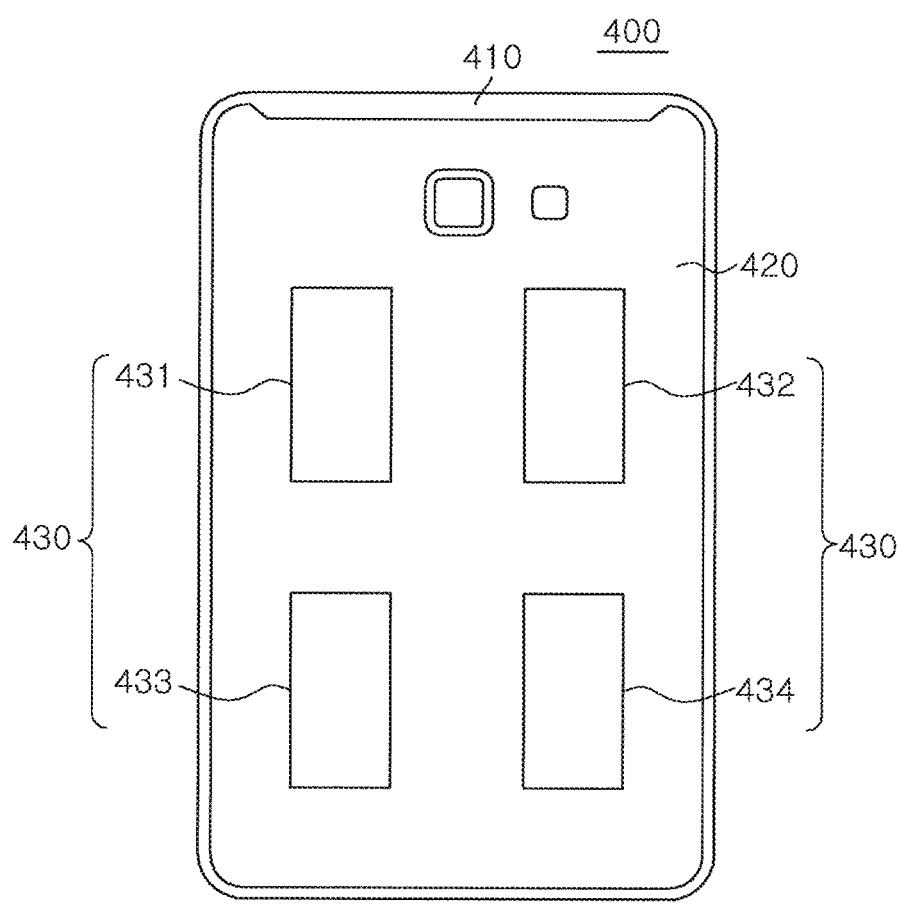
FIG. 20 illustrates a diagram of an example terminal configured to communicate with a refrigerator according to still another embodiment.
Figure 21:
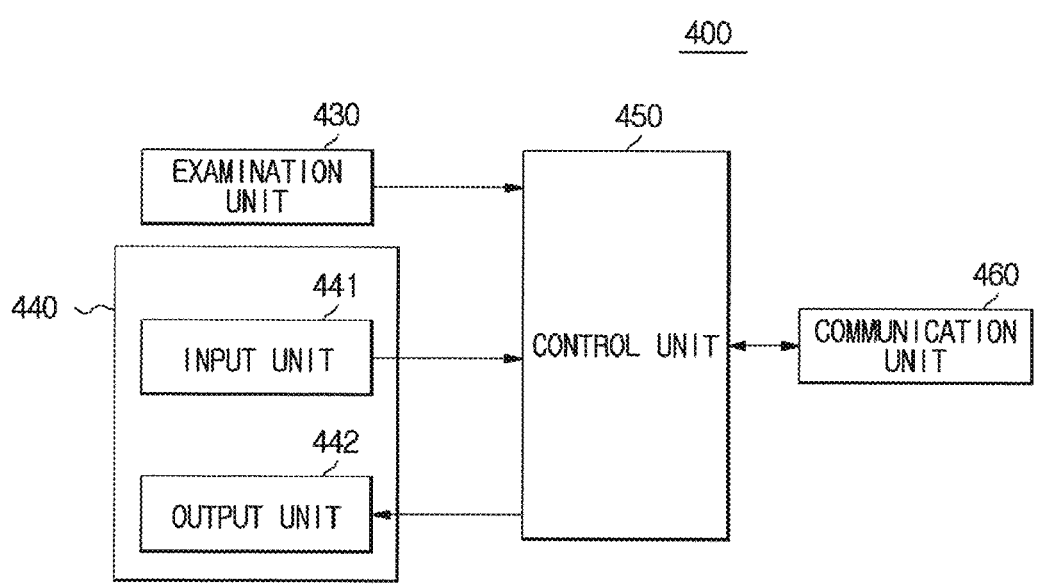
FIG. 21 illustrates a control configuration diagram of a terminal configured to communicate with a refrigerator according to still another embodiment.

FIG. 20 is a diagram of an example smartphone serving as the terminal. FIG. 21 is a control configuration diagram of a smartphone serving as the terminal. The smartphone serving as the terminal includes a main body, a call function, an Internet communication function, an information search function, and further includes a health examination function.

A terminal 400 includes a main body 410, a cover 420 covering a rear surface of the main body 410, and at least one conductive electrode 431, 432, 433, or 434 that is provided in the cover 420 and serves as an examination unit 430 configured to measure a bio signal.

When the examination unit is provided in the cover in this manner, it is possible to measure the bio signal without increasing a thickness and a size of the terminal. Also, since it is possible for the examination unit 430 to access a battery of the terminal, power may be provided from the battery of the terminal.

The bio signal is an electrical signal that may be generated when an electrochemical change is generated in nerve cells and muscle cells.

Here, when the conductive electrode comes in contact with a body, the electrical signal measured in the body may be detected. When the detected signal is processed, the bio signal may be measured.

Further, the conductive electrode may measure the body fat percentage or the electrocardiogram of the body.

The conductive electrode delivers a current to the body and measures an amount of change in resistance in the body such that at least one bio signal may be measured.

When a fine alternating current signal is delivered to the body, different impedances are generated in body fat, muscles, water, and the like. When a body impedance is measured using this difference, a body fat mass may be measured. At least four conductive electrodes may be used for this measurement.

Also, the conductive electrode may measure an electrocardiographic signal having electrical properties that are generated along with a heartbeat of the body.

That is, electrocardiography (ECG) is a technique in which an electrical activity generated in the heart is obtained by an electrode attached on the skin and a change over time is displayed. Measurement by electrocardiography may be performed using at least two electrodes out of four electrodes.

Measurement by electrocardiography may be performed by observing a change in a fine electrical signal generated by depolarization whenever muscles in the heart contract and amplifying the signal.

The examination unit is not limited thereto, but may further include other components configured to measure a bio signal, for example, a temperature sensor, and an optical sensor.

The temperature sensor may measure a body temperature.

The optical sensor may measure a pulse wave or an oxygen saturation level of the body. The optical sensor radiates light into the body through the body skin and then detects transmitted light in a light receiving unit. Therefore, the pulse wave or the oxygen saturation level may be measured.

Accordingly, the optical sensor configured to measure a bio signal may include a light-emitting sensor for generating light and a light-receiving sensor for absorbing light transmitted from the body. The optical sensor includes the light-receiving sensor and the light-emitting sensor having at least one wavelength, and may detect the bio signal such as the pulse wave and the oxygen saturation level.

The terminal further includes an input/output unit 440 configured to receive an examination command and output an examination result, a control unit 450 configured to control overall operations of the examination unit, and a communication unit 460 configured to communicate with the refrigerator.

The input/output unit 440 includes an input unit 441 configured to receive the examination command and a transmission command of the examined health information and receive user information and an output unit 442 configured to output the examined health information and output a result indicating whether the health information is transmitted.

Also, a display serving as the output unit 442 of the terminal may display an examination method and the like.

The control unit 450 converts the bio signal measured in the examination unit 430 into an electrical signal and delivers the converted signal to the refrigerator 100.

The control unit 450 analyzes the measured electrocardiographic signal, determines whether the signal is normal, and may also deliver data including the determination result to the refrigerator.

Also, the control unit 450 may filter the bio signal measured in the examination unit 430 or analyze the bio signal using various methods such as detection of an electrocardiographic beat, detection of a pulse wave beat, calculation of the number of heartbeats, detection of arrhythmia, calculation of pulse wave arrival time, extraction of a level of a blood vessel state, calculation of an oxygen saturation level, and calculation of a body fat percentage.

The control unit 450 identifies the examination time when the examination is performed and controls transmission of the identified examination time and the examined health information.

The communication unit 460 performs communication with the refrigerator, and when a health information command is received, transmits the health information and the examination time to the refrigerator.

Configurations of the user interface unit 140, the control unit 150, and the storage unit 160 that are the same as those in the previous embodiments will not be described. In other words, description will be provided focusing on a configuration related to the communication unit 170.

Figure 22:
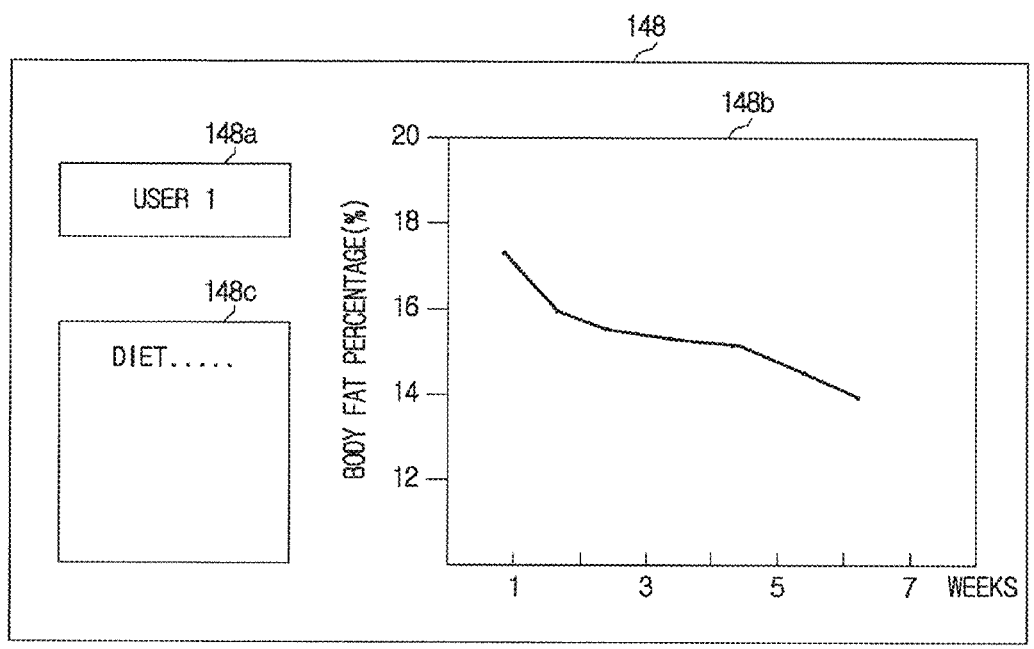
FIG. 22 illustrates an example of a user interface unit included in a refrigerator according to still another embodiment.

As illustrated in FIG. 22, when health information is received from the external device, the user interface unit 140: 148 displays the received health information.

When the health information is received from the external device, the user information may also be received and the user information may also be received through the user interface unit.

The user interface unit displays user information 148a and the received health information along with accumulated and stored health information 148b, and displays notification information 148c corresponding to the analyzed health state over the examination time.

When the health information transmitted from the external device is received through the communication unit 170, the control unit 150 accumulates and stores the received health information in the storage unit.

In this embodiment, the control unit 150 accumulates and stores the input health information and the received health information for each examination item.

In addition, the control unit 150 may directly receive food information using the grocery manager in the input unit of the user interface unit and may also perform control such that the order list is transmitted to the food server.

The control unit 150 manages food and provides the accumulated health information to the user the same according to the previous embodiment.

The storage unit 160 matches the received health information and the user information, and stores in order of the examination time.

FIG. 23 is a control flowchart of a refrigerator according to still another embodiment.

Configurations that are the same as those in the previous embodiments are briefly described.

The refrigerator controls the freezing cycle, keeps an interior temperature of the storage container at a target temperature, and therefore keeps food stored in each storage container fresh.

In this embodiment, information on food stored in each storage container is previously stored in the storage unit 160.

Here, the information on food includes a food name, information on food having an expiration date, and information on the storage location of food. Management of the food may be performed by the method illustrated in FIGS. 5 to 8.

The user interface unit of the refrigerator maintains a waiting state and determines whether the health information is received from the external device (521). When it is determined that the health information is received from the external device, the determined received health information is added to and stored in the storage unit (522).

Here, when the health information is received, the examination time at which health information is examined is also received.

Also, in reception of the health information, when the examination time is not received, a reception time at which the health information is received may also be replaced with the examination time and stored.

In this embodiment, the health information is accumulated and stored in the previously stored health information. User information of the received health information is identified. The identified user information and the health information are matched and stored.

In addition, the user information may be directly received through the user interface unit.

The user interface unit of the refrigerator maintains a waiting state and determines whether the health care mode is input (523). That is, when the user touches the health care button of the menu window of the user interface unit, a mode enters the health care mode.

The refrigerator switches a current mode to the health care mode and displays user information of a pre-registered user for performing the health care mode in this embodiment (refer to FIG. 9).

Here, display of the user information includes display of the user's name or ID in the form of a button.

The refrigerator receives selection of any user among the pre-registered users (524).

That is, when any button on which user information is displayed among the pre-registered users is touched, the refrigerator determines user information of the touched location.

Then, the refrigerator displays user information of the selected user and the examination item (refer to FIG. 10).

Then, when the user touches any examination item button, the refrigerator extracts and outputs accumulated health information of the touched examination item (525).

When the examination item is, for example, a blood pressure, the user interface unit 140 displays blood pressures from an initially input blood pressure to a most recently input blood pressure in order of the examination time When the user inputs the health information and the examination time, the refrigerator may also add and store currently input health information to previously accumulated and stored health information.

Also, when health information is input, if the examination time is not input, an input time at which health information is input may also be replaced with the examination time and stored.

When the examination period is selected by the user, the refrigerator may also extract and display health information within the selected examination period. In this embodiment, health information of the selected examination item may also be displayed.

Then, the refrigerator analyzes the accumulated and stored health information, determines his or her health state, and provides notification information of the determined health state as a guidance note.

Then, the refrigerator analyzes the accumulated and stored health information, determines his or her health state, and provides a service for the user's health promotion based on the determined health state. In this embodiment, when there is a plurality of examination items, the accumulated and stored health information is extracted for each of the plurality of examination items and various pieces of health information are comprehensively analyzed.

That is, the refrigerator searches for food that is good for the user to eat based on the accumulated and stored health information and information on food stored in the storage container (526), generates and displays the recommended dish menu made of the found food, and identifies and displays prohibited food that is not good for the user to eat based on the accumulated and stored health information and the information on food stored in the storage container (refer to FIG. 13).

Here, when the recommended dish menu is generated, the menu is generated based on an expiration date of food used for the dish, and a dish using food having an imminent expiration date is set to have a high display priority.

Also, the refrigerator adds food to a wish list and displays the food that is food made of a food material that is not stored in the storage container among food materials necessary for cooking a dish of the recommended dish menu and is recommend to be purchased. Food selected by the user from among food in the wish list is recognized as food for an order and the recognized food is added to the order list and displayed (516).

For example, when it is determined that a carrot necessary for cooking bulgogi among the recommended dish menu is not stored in the storage container, the carrot is added to the wish list. When the carrot is selected in the wish list, the carrot is added to the order list.

Then, the refrigerator determines whether a food order request button is input. When it is determined that the food order request button is input, the refrigerator transmits a food order request signal to the food server 200. In this embodiment, food information of the order list and the user information are transmitted together (527).

Also, without a food selection process by the user, it is possible to automatically order food from the food server.

After the order is completed, when food information of delivered food is received from the food server, the refrigerator stores the received food information.

Then, the refrigerator identifies a location of an empty space among an area of the storage container, determines a storage location that is appropriate to store the purchased food based on the received food information and the location of the empty space, displays the determined storage location through the user interface unit, and therefore the appropriate storage location of the purchased food may also be provided to the user.

In addition, when the user stores the purchased food in the storage container, if the food information and the recommended storage location are selected together, the selected storage location and the food information are matched, and the matching storage location and food information are stored in the storage unit 160.

Also, the user may arbitrarily select the storage location of food.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method of controlling a refrigerator having a user interface unit, the method comprising:
    receiving information on a user;
    receiving health information of the user and an examination time;
    matching and storing the health information and examination time being received;
    displaying the health information in order of the examination time;
    comparing the stored health information in order of the examination time, and analyzing and displaying a change in a health state of the user;
    generating a recommended dish menu based on the analyzed change in the health state and food stored in a storage container; and
    displaying the generated recommended dish menu.

2. The method according to claim 1, further comprising receiving the health information and the examination time transmitted from an external device, and
    matching and storing the health information and the examination time being received.

3. The method according to claim 2, further comprising responsive to the examination time not being received in reception of the health information from the external device, matching and storing a reception time at which the health information is received and the health information.

4. The method according to claim 1, further comprising, responsive to a plurality of users, matching user information of each user and health information for each examination time and storing.

5. The method according to claim 1, further comprising receiving food information and a storage location of food to be stored in the storage container; and
    matching and storing the received food information and the storage location.

6. The method according to claim 1, wherein the generating of the recommended dish menu includes:
    identifying an expiration date among the stored food information; and generating the recommended dish menu based on the identified expiration date of food.

7. The method according to claim 6, wherein the displaying of the generated recommended dish menu includes:
identifying food used for each recommended dish in the generated recommended dish menu;
identifying an expiration date of the identified food; and
determining a display priority of the recommended dish menu such that a recommended dish menu made of food having the shortest expiration date among the identified expiration dates is set to a top priority.

8. The method according to claim 1, further comprising:
identifying prohibited food based on the health information and the health state being stored, and food information stored in a storage unit; and
displaying the identified prohibited food.

9. The method according to claim 1, further comprising:
receiving deletion of information on food removed from the storage container; and
deleting information on food of which removal is received from the stored food information.

10. The method according to claim 1, further comprising:
identifying food used for the recommended dish menu;
comparing the identified food with the stored food information and identifying food that is not in the storage container among the identified food;
adding and storing the identified food to a wish list; and
displaying the wish list.

11. The method according to claim 10, further comprising transmitting food selected by the user among the wish list to a food server.

* * * * *